(12) United States Patent
Smith-Swintosky et al.

(10) Patent No.: US 8,716,231 B2
(45) Date of Patent: *May 6, 2014

(54) USE OF BENZO-FUSED HETEROCYCLE SULFAMIDE DERIVATIVES FOR THE TREATMENT OF PAIN

(75) Inventors: Virginia L. Smith-Swintosky, Hatfield, PA (US); Allen B. Reitz, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 179 days.

This patent is subject to a terminal disclaimer.

(21) Appl. No.: 11/612,071

(22) Filed: Dec. 18, 2006

(65) Prior Publication Data

US 2007/0155822 A1 Jul. 5, 2007

Related U.S. Application Data

(60) Provisional application No. 60/751,686, filed on Dec. 19, 2005, provisional application No. 60/773,812, filed on Feb. 15, 2006.

(51) Int. Cl.
- A61K 31/335 (2006.01)
- A01N 43/32 (2006.01)
- A61K 31/80 (2006.01)
- A01N 43/26 (2006.01)

(52) U.S. Cl.
USPC .......... 514/18.2; 514/452; 514/456; 514/463; 514/465

(58) Field of Classification Search
None
See application file for complete search history.

(56) References Cited

U.S. PATENT DOCUMENTS

| | | |
|---|---|---|
| 2,527,861 A | 10/1950 | Walter |
| 3,143,549 A | 8/1964 | Lafferty et al. |
| 3,318,952 A | 5/1967 | Houlihan |
| 3,383,414 A | 5/1968 | Houlihan |
| 3,539,573 A | 11/1970 | Schmutz |
| 3,621,096 A | 11/1971 | Prange et al. |
| 4,513,006 A | 4/1985 | Maryanoff et al. |
| 4,539,413 A | 9/1985 | Mouzin et al. |
| 4,710,500 A | 12/1987 | Perregaard |
| 4,804,663 A | 2/1989 | Kennis et al. |
| 4,831,031 A | 5/1989 | Lowe, III et al. |
| 4,879,288 A | 11/1989 | Warawa et al. |
| 5,112,838 A | 5/1992 | Perregaard et al. |
| 5,158,952 A | 10/1992 | Janssen et al. |
| 5,192,785 A | 3/1993 | Lo et al. |
| 5,194,446 A | 3/1993 | Lo et al. |
| 5,212,326 A | 5/1993 | Meade |
| 5,229,382 A | 7/1993 | Chakrabarti et al. |
| 5,238,945 A | 8/1993 | Perregaard et al. |
| 5,242,942 A | 9/1993 | Costanzo et al. |
| 5,258,402 A | 11/1993 | Maryanoff |
| 5,273,993 A | 12/1993 | Lo et al. |
| 5,312,925 A | 5/1994 | Allen et al. |
| 5,384,327 A | 1/1995 | Costanzo et al. |
| 5,387,700 A | 2/1995 | Maryanoff et al. |
| 5,731,348 A | 3/1998 | Gu et al. |
| 5,753,693 A | 5/1998 | Shank |
| 5,753,694 A | 5/1998 | Shank |
| 5,760,007 A | 6/1998 | Shank et al. |
| 5,780,650 A | 7/1998 | Furukawa et al. |
| 5,935,933 A | 8/1999 | Shank et al. |
| 5,998,380 A | 12/1999 | Ehrenberg et al. |
| 6,071,537 A | 6/2000 | Shank |
| 6,150,419 A | 11/2000 | Fairbanks et al. |
| 6,187,338 B1 | 2/2001 | Caruso et al. |
| 6,191,163 B1 | 2/2001 | Coltrell |
| 6,211,241 B1 | 4/2001 | Islam et al. |
| 6,319,903 B1 | 11/2001 | Carrazana et al. |
| 6,322,503 B1 | 11/2001 | Sparhawk, Jr. |
| 6,323,236 B2 | 11/2001 | McElroy |
| 6,391,877 B1 | 5/2002 | Islam et al. |
| 6,503,884 B1 | 1/2003 | Ehrenberg et al. |
| 6,559,293 B1 | 5/2003 | Almarsson et al. |
| 6,562,865 B1 | 5/2003 | Codd et al. |
| 6,583,172 B1 | 6/2003 | Shank |
| 6,627,653 B2 | 9/2003 | Plata-Salaman et al. |
| 6,852,701 B2 | 2/2005 | Plata-Salaman et al. |
| 6,852,738 B2 | 2/2005 | Jones et al. |
| 6,949,518 B1 | 9/2005 | Chu |
| 2001/0008889 A1 | 7/2001 | Caruso et al. |
| 2002/0015713 A1 | 2/2002 | Murdock et al. |
| 2004/0073037 A1 | 4/2004 | Jones et al. |

(Continued)

FOREIGN PATENT DOCUMENTS

| | | |
|---|---|---|
| CA | 2 416 647 A | 1/2003 |
| DE | 1211166 | 2/1966 |

(Continued)

OTHER PUBLICATIONS

Olson et al [Editors]. Remington's Pharmaceutical Sciences. pp. 420-425, 1980.*
Dickenson et al. Neurobiology of neuropathic pain: mode of action of anticonvulsants. European Journal of Pain, 2002, 6 (Suppl. A): 51-60, 2002.*
Burton et al. Anti-epileptic drugs for pain management. Pain, Symptom, Control and Palliative Care, 2001, vol. 1, No. 2.*
Maryanoff et al: Anticonvulsant O-Alkyl Sulfamates 2,3:4,5-Bis-O-(1-methylethylidene)-betas-D-fructopyranose Sulfamate and Related Compounds*, J.Med. Chem., vol. 30, No. 5, 1987, pp. 880-887.

(Continued)

Primary Examiner — Anna Pagonakis
(74) Attorney, Agent, or Firm — Hal B. Woodrow

(57) ABSTRACT

The present invention is a method for the treatment of pain comprising administering to a subject in need thereof a therapeutically effective amount of one or more novel benzo-fused heterocycle sulfamide derivatives of formula (I) and formula (II) as described herein. The present invention is further directed to methods for the treatment of pain comprising co-therapy with analgesic agent(s) and a compound of formula (I) or formula (II) as described herein.

9 Claims, No Drawings

(56) References Cited

U.S. PATENT DOCUMENTS

| | | |
|---|---|---|
| 2004/0192690 A1 | 9/2004 | Buxton et al. |
| 2004/0253223 A1 | 12/2004 | Rodriguez |
| 2005/0148603 A1 | 7/2005 | Jimenez et al. |
| 2005/0282887 A1 | 12/2005 | McComsey et al. |
| 2006/0047001 A1 | 3/2006 | Parker et al. |
| 2006/0241172 A1 | 10/2006 | Zhou et al. |
| 2006/0270856 A1 | 11/2006 | Abdel-Magid |
| 2006/0276528 A1 | 12/2006 | Parker et al. |
| 2007/0293440 A1 | 12/2007 | Smith-Swintosky et al. |
| 2007/0293476 A1 | 12/2007 | Smith-Swintosky et al. |
| 2009/0182141 A1 | 7/2009 | Abdel-Magid et al. |
| 2009/0209634 A1 | 8/2009 | Smith-Swintosky |
| 2009/0247617 A1 | 10/2009 | Abdel-Magid et al. |
| 2009/0247618 A1 | 10/2009 | Ballentine et al. |
| 2009/0318544 A1 | 12/2009 | Mehrman et al. |
| 2010/0063138 A1 | 3/2010 | McComsey et al. |

FOREIGN PATENT DOCUMENTS

| | | |
|---|---|---|
| DE | 2022370 | 12/1971 |
| DK | 9800727 A | 5/1998 |
| EP | 0138441 B1 | 4/1985 |
| EP | 0483881 B1 | 5/1992 |
| EP | 490689 | 6/1992 |
| EP | 498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2246727 | 4/2004 |
| RU | 2226357 | 8/2004 |
| WO | WO 94/14827 A1 | 7/1994 |
| WO | WO 95/17406 A1 | 6/1995 |
| WO | WO 96/06822 A1 | 3/1996 |
| WO | WO 97/13510 A1 | 4/1997 |
| WO | WO 97/19682 A1 | 6/1997 |
| WO | WO 97/19919 | 6/1997 |
| WO | WO 97/35584 A1 | 10/1997 |
| WO | WO 98/00123 | 1/1998 |
| WO | WO 98/00124 A1 | 1/1998 |
| WO | WO 98/00130 A2 | 1/1998 |
| WO | WO 98/00131 A1 | 1/1998 |
| WO | WO 98/06708 A1 | 2/1998 |
| WO | WO 98/07447 A1 | 2/1998 |
| WO | WO 98/15270 | 4/1998 |
| WO | WO 99/44581 A2 | 9/1999 |
| WO | WO 99/62522 | 12/1999 |
| WO | WO 00/01376 A2 | 1/2000 |
| WO | WO 00/07583 A2 | 2/2000 |
| WO | WO 00/42995 A2 | 7/2000 |
| WO | WO 00/42996 A2 | 7/2000 |
| WO | WO 00/49017 | 8/2000 |
| WO | WO 00/50020 A2 | 8/2000 |
| WO | WO 00/54588 A1 | 9/2000 |
| WO | WO 00/61137 | 10/2000 |
| WO | WO 00/61139 A1 | 10/2000 |
| WO | WO 00/61140 A1 | 10/2000 |
| WO | WO 00/66109 A2 | 11/2000 |
| WO | WO 00/76493 A1 | 12/2000 |
| WO | WO 01/13904 A2 | 3/2001 |
| WO | WO 01/76576 A2 | 10/2001 |
| WO | WO 02/03984 | 1/2002 |
| WO | WO 02/07821 A | 1/2002 |
| WO | WO 02/09694 | 2/2002 |
| WO | WO 02/30881 | 4/2002 |
| WO | WO 02/089785 | 11/2002 |
| WO | WO 02/096424 A1 | 12/2002 |
| WO | WO 2004/014352 | 2/2004 |
| WO | WO 2004/093912 A1 | 4/2004 |
| WO | WO 2004/092116 A1 | 10/2004 |
| WO | WO 2004/096771 A1 | 11/2004 |
| WO | WO 2004/098584 A1 | 11/2004 |
| WO | WO 2005/0020917 A2 | 3/2005 |
| WO | WO 2006/007435 | 1/2006 |
| WO | WO 2006/007436 | 1/2006 |
| WO | WO 2006/010008 A1 | 1/2006 |
| WO | WO 2006/010750 A1 | 2/2006 |
| WO | WO 2006/023861 A1 | 3/2006 |
| WO | WO 2006/127184 | 11/2006 |
| WO | WO 2007/075695 | 7/2007 |
| WO | WO 2007/075698 | 7/2007 |
| WO | WO 2007/075717 | 7/2007 |
| WO | WO 2007/075751 | 7/2007 |
| WO | WO 2007/075752 | 7/2007 |
| WO | WO 2007/075833 | 7/2007 |
| WO | WO 2007/075834 | 7/2007 |
| WO | WO 2007/092086 | 8/2007 |
| WO | WO 2007/095615 | 8/2007 |
| WO | WO 2007/095618 | 8/2007 |
| WO | WO 2007/098486 | 8/2007 |
| WO | WO 2007/137167 | 11/2007 |
| WO | WO 2009/089210 | 7/2009 |
| WO | WO 2009/120191 | 10/2009 |
| WO | WO 2009/120192 | 10/2009 |

OTHER PUBLICATIONS

Maryanoff et al: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.

Rost et al: The Effect of Tramadol and other analgesics on the pain . . . , English Abstract Arzneim-Forsch. 1978, vol. 28 1a0, pp. 181-183.

Dressler et al: Benzodiazepine in geriatric patients . . . , English Abstract, Anaesthesiologie und reanimation, 1996, vol. 21/5, pp. 136-138.

Kralinsky E.A. Tramal in the treatment of pain in children with malignancies XP002162259 English Abstract & Klinicka Onkologie, vol. 7, No. 6, 1994, pp. 182-185.

Grond et al: "ek opiods—an educational substitute for morphine?" Current Opinion in Anaesthesiology, vol. 11, No. 5, 1998, pp. 559-565 XP000982759.

Scozzafava A et al, "Modulaton of Carbonic Anhydrase Activity and Its Applications in Therapy", Expert Opinion on Therapeutic Patents 2003 United Kingdom,vol. 14, No. 5 (2004) pp. 667-702, XP002331413, ISSN:1354-3776.

Polomano et al: "A painful peripheral neuropathy in the rat produced by the chemotherapeutic drug, paclitaxel", Pain, 94:293-304, 2001.

Flatters, SJL et al: "Acetyl-L-camitine prevents and reduces paclitaxel-induced painful peripheralneuropathy", Neurosci Lett 397:219-223, 2006.

Chaplan SR et al: "Quantitative assessment of tactile allodynia in the rat paw". J Neurosci Meth, 53:55-63, 1994.

Cavaletti G et al: "Experimental peripheral neuropathy induced in adult rats by repeated intraperitoneal administration of Taxal", Exper Neurol 133:64-72, 1995.

Pascual D et al: "A cannabinoid agonist, WIN55,212-2, reduces neuropathic nocicipetion induced by paclitaxel in rats" Pain 118:23-34, 2005.

U.S. Appl. No. 11/154,443, Maryanoff, Bruce E.
U.S. Appl. No. 11/154,386, McComsey, David F.
U.S. Appl. No. 11/209,122, Maryanoff, Bruce E.
U.S. Appl. No. 11/611,938, Smith-Swintosky.
U.S. Appl. No. 11/611,961, Reitz, Allen B.
U.S. Appl. No. 11/612,146, Reitz, Allen B.
U.S. Appl. No. 11/612,174, Smith-Swintosky.
U.S. Appl. No. 11/612,202, Reitz, Allen B.
U.S. Appl. No. 11/612,222, Smith-Swintosky.
U.S. Appl. No. 11/612,249, Reitz, Allen B.
U.S. Appl. No. 11/673,705, Smith-Swintosky.
U.S. Appl. No. 11/673,709, Smith-Swintosky.
U.S. Appl. No. 11/673,713, Smith-Swintosky.
U.S. Appl. No. 11/673,723, Smith-Swintosky.
PCT International Search Report, PCT/US2005/029814, Nov. 9, 2005, U.S. Appl. No. 11/209,122.
PCT International Search Report, PCT/US2005/021513, Sep. 27, 2005, U.S. Appl. No. 11/154,443.

(56) References Cited

OTHER PUBLICATIONS

PCT International Search Report, PCT/US2005/021515, Jun. 16, 2005, U.S. Appl. No. 11/154,386.
PCT International Search Report, PCT/US2006/048681, Jul. 5, 2007, U.S. Appl. No. 11/611,938.
U.S. Appl. No. 11/673,977, Smith-Swintosky.
U.S. Appl. No. 11/873,987, Smith-Swintosky.
U.S. Appl. No. 11/673,998, Smith-Swintosky.
U.S. Appl. No. 11/674,011, Smith-Swintosky.
U.S. Appl. No. 11/674,021, Smith-Swintosky.
U.S. Appl. No. 11/677,717, Fawzy Nagy.
U.S. Appl. No. 60/883,442, Smith-Swintosky.
Migraine: Treatments and drugs, by Mayo Clinic Staff, http://www.mayoclinic.com/health/migraine-headache/DS00120/DSECTION=treatments-and-drugs.
Office Action mailed Mar. 26, 2008 in U.S. Appl. No. 11/154,443.
Notice of Allowance mailed Dec. 31, 2008 in U.S. Appl. No. 11/154,443.
Notice of Allowance mailed Jun. 8, 2009 in U.S. Appl. No. 11/154,443.
Notice of Allowance mailed Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated May 4, 2011 in U.S. Appl. No. 11/154,443.
Notice of Allowance dated Aug. 12, 2011 in U.S. Appl. No. 11/154,443.
Office Action mailed Oct. 3, 2007 in U.S. Appl. No. 11/154,386.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Notice of Allowance dated Feb. 23, 2010 in U.S. Appl. No. 11/154,386.
Notice of Allowance dated Oct. 22, 2010 in U.S. Appl. No. 11/154,386.
Office Action mailed Apr. 14, 2008 in U.S. Appl. No. 11/209,122.
Notice of Allowance mailed Oct. 30, 2008 in U.S. Appl. No. 11/209,122.
Office Action mailed Mar. 20, 2009 in U.S. Appl. No. 11/209,122.
Notice of Allowance mailed Sep. 24, 2009 in U.S. Appl. No. 11/209,122.
Notice of Allowance mailed Jan. 13, 2010 in U.S. Appl. No. 11/209,122.
Notice of Allowance mailed Jan. 11, 2011 in U.S. Appl. No. 11/209,122.
Notice of Allowance mailed Jun. 1, 2011 in U.S. Appl. No. 11/209,122.
Notice of Allowance mailed Oct. 18, 2011 in U.S. Appl. No. 11/209,122.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.
Notice of Allowance dated Nov. 29, 2010 in U.S. Appl. No. 11/406,794.
Notice of Allowance dated Mar. 14, 2011 in U.S. Appl. No. 11/406,794.
Notice of Allowance dated Jun. 30, 2011 in U.S. Appl. No. 11/406,794.
Corrected Notice of Allowance dated Jul. 20, 2011 in U.S. Appl. No. 11/406,794.
Notice of Allowance dated Oct. 4, 2011 in U.S. Appl. No. 11/406,794.
Office Action mailed Aug. 17, 2009 in U.S. Appl. No. 11/611,938.
Final Office Action mailed Feb. 25, 2010 in U.S. Appl. No. 11/611,938.
Office Action mailed May 2, 2008 in U.S. Appl. No. 11/611,961.
Final Office Action mailed Jan. 29, 2009 in U.S. Appl. No. 11/611,961.
Notice of Allowance dated Jun. 2, 2009 in U.S. Appl. No. 11/611,961.
Notice of Allowance dated Jan. 6, 2010 in U.S. Appl. No. 11/611,961
Notice of Allowance dated Apr. 30, 2010 in U.S. Appl. No. 11/611,961.
Notice of Allowance dated Aug. 12, 2010 in U.S. Appl. No. 11/611,961.
Notice of Allowance dated Nov. 30, 2010 in U.S. Appl. No. 11/611,961.
Notice of Allowance dated Mar. 14, 2011 in U.S. Appl. No. 11/611,961.
Notice of Allowance dated Jul. 18, 2011 in U.S. Appl. No. 11/611,961.
Notice of Allowance dated Oct. 26, 2011 in U.S. Appl. No. 11/611,961.
Final Office Action mailed Aug. 5, 2008 in U.S. Appl. No. 11/612,146.
Final Office Action mailed Oct. 29, 2009 in U.S. Appl. No. 11/612,146.
Office Action mailed Jan. 29, 2009 in U.S. Appl. No. 11/612,174.
Office Action mailed Jul. 11, 2011 in U.S. Appl. No. 12/431,141.
Office Action mailed Dec. 15, 2011 in U.S. Appl. No. 12/431,141.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Notice of Allowance mailed Nov. 15, 2010 in U.S. Appl. No. 11/612,202.
Notice of Allowance mailed Mar. 4, 2011 in U.S. Appl. No. 11/612,202.
Notice of Allowance dated Sep. 19, 2011 in U.S. Appl. No. 11/612,202.
Office Action mailed Jul. 9, 2010 in U.S. Appl. No. 11/612,222.
Office Action mailed Apr. 12, 2011 in U.S. Appl. No. 11/612,222.
Office Action mailed Oct. 4, 2011 in U.S. Appl. No. 11/612,222.
Office Action mailed Jul. 21, 2009 in U.S. Appl. No. 11/612,249.
Final Office Action mailed Jan. 28, 2010 in U.S. Appl. No. 11/612,249.
Office Action mailed Oct. 15, 2010 in U.S. Appl. No. 11/612,249.
Office Action mailed Apr. 22, 2011 in U.S. Appl. No. 11/612,249.
Office Action mailed Oct. 6, 2011 in U.S. Appl. No. 10/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Notice of Allowance mailed Dec. 15, 2010 in U.S. Appl. No. 11/674,021.
Notice of Allowance dated Aug. 22, 2011 in U.S. Appl. No. 11/674,021.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Notice of Allowance mailed Dec. 15, 2010 in U.S. Appl. No. 11/750,600.
Office Action/Interview Summary dated Sep. 1, 2011 in U.S. Appl. No. 11/750,600.

(56) References Cited

OTHER PUBLICATIONS

Notice of Allowance dated Sep. 12, 2011 in U.S. Appl. No. 11/750,600.
Notice of Allowance dated Dec. 22, 2011 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action mailed Sep. 22, 2010 in U.S. Appl. No. 12/055,433.
Office Action mailed Jun. 8, 2011 in U.S. Appl. No. 12/055,433.
Office Action mailed Dec. 22, 2011 in U.S. Appl. No. 12/055,433.
Office Action mailed May 26, 2011 in U.S. Appl. No. 12/055,695.
Office Action mailed Jul. 15, 2011 in U.S. Appl. No. 12/055,695.
Final Office Action mailed Nov. 21, 2011 in U.S. Appl. No. 12/055,695.
Office Action mailed Nov. 15, 2010 in U.S. Appl. No. 12/055,924.
Notice of Allowance mailed Apr. 12, 2011 in U.S. Appl. No. 12/055,924.
Office Action mailed Oct. 6, 2011 in U.S. Appl. No. 12/349,184.
Office Action mailed Jun. 1, 2010 in U.S. Appl. No. 12/488,079.
Notice of Allowance mailed Dec. 14, 2010 in U.S. Appl. No. 12/488,079.
Notice of Allowance mailed Jun. 21, 2011 in U.S. Appl. No. 12/488,079.
Notice of Allowance dated Nov. 1, 2011 in U.S. Appl. No. 12/488,079.
Office Action mailed Jul. 8, 2011 in U.S. Appl. No. 12/502,472.
Notice of Allowance dated Nov. 28, 2011 in U.S. Appl. No. 12/502,472.
International Search Report re: PCT/US2006/048539 dated May 23, 2007.
O'Donnell et al., Chapter 15, "Drug Therapy of Depression and Anxiety Disorders", Goodman & Gilman's The Pharmacological Basis of Therapeutics, 12th Edition, 2011, pp. 397-415.
McNamara, J., Chapter 21, "Pharmacotherapy of the Epilepsies", Goodman & Gilman's The Pharmacological Basis of Therapeutics, $12^{th}$ Edition, 2011, pp. 583-607.
Aeberli, P. et al. "Neuropharmacological Investigation of N-Benzylsulfamides", Journal of Medicinal Chemistry, Jul. 1967, vol. 10, No. 4, pp. 636-642.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Ayata et al., "Suppression of cortical Spreading Depression in Migraine Prophylaxis", Ann Neurol 2006; 59:652-661.
Barry et al. Current status of the utilization of antiepipleptic treatments in mood, anxiety and aggression: drugs and devices, Jan. 2004, 35, 1.
Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):S78-84.
Berman, R.M. et al., Depress. Anxiety 1997, 5, 154-164.
Besag et al. "Behavioural Effects of the New Anticonvulsants" Drug Safety, ADIS Press, Auckland, NZ, vol. 24, No. 7, 2001, pp. 513-536.
Breslau et al., "The impact of migraine. Epidemiology, risk factors, and comorbidities" Neurology, 2001;56:S4-S12 (Abstract only).
Cadieux, R.J., Am. Fam. Physician 1998, 58, 2059-2062.
Calabrese, J.R. et al., Eur. Neuropsychopharmacol. 1999, 9, S109-S112.
Calabresi et al., "Antiepileptic drugs in migraine: from clinical aspects to cellular mechanisms", Trends in Pharmacological Sciences, vol. 28, No. 4, 188-195 (2007).

Caumo A., "Insulin Sensitivity from Meal Tolerance Tests in Normal Subjects: A Minimal Model Index", J Clin Endocrinol Metab, 85(11):4396-402 2000.
Crooke et al, Abstract, Topiramate Improves Glycemic Control Independent of Weight Loss in ob/ob Mice.diabetes. A Journal of the American Diabetes Association, Abstract Book 61st Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dinneen S.F., "The Postprandial State: Mechanism of Glucose Intolerance", Diabet Med Aug. 1997;14 Suppl 3:S19-24.
Drach, B.S. et al.:"N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.
Drug Facts and Comparison (1995 Edition, pp. 1607).
Dursun, S.M. et al., "Accelerated weight loss after treating refractory depression with fluoxetine plus topiramate: possible mechanisms of action?", the Canadian Journal of Psychiatry, vol. 46, No. 3, pp. 287-288, 2001.
Edwards, K.R. et al, Efficacy and safety of topiramate in the treatment of painful diabetic neuropathy: a double-blind placebo-controlled study ADIS Title: Topiramate: therapeutic use: Neurogenic pain; in patients with diabetic neuropathy: Neurology 54 (Suppl. 3): 81 Apr. 11, 2000.
Edwards, et al., Evaluation of Topiramate in the Management of Painful Diabetic Neuropathy. Presented at: $18^{th}$ Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behay. Aug. 2007, abstract.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obesity; In patient with binge eating disorders" International Journal of Neuropsychopharmacology 3(Suppl 1): 299: Jul. 2000 XP001030426 Bassano dG Vicenza Italy, whole document.
Ghaemi et al., Soc. of Bio. Psychiatry, (1999) vol. 45, 137-144.
Goldberg R.G., "Prevention of Type 2 Diabetes", Med Clin North Am, Jul. 1998;82(4):805-21.
Gorelick DA, "Pharmacological treatment" Recent Developments in Alcoholism, vol. 11, 1993, p. 413-427, XP00913482 p. 417.
Gorelick et al., Drugs 2004: 64(14), pp. 1547-1573.
Groop L., "Characterization of the Prediabetic State", Am J Hypertension; Sep. 1997;10(9 Pt 2):172S-180S.
Guillaume et al., "Glial contribution to seizure: Carbonic anhydrase activity in epileptic mammalian brain" Epilepsia, 1991, vol. 32, No. 1, 1991, pp. 10-15.
Haffner S.M., "Impaired Glucose Tolerance, Insulin Resistance and Cardiovascular Disease", Diabetic Medicine, Aug. 1997;14 Suppl 3:S12-8.
Haffner S.M., "The Prediabetic Problem: Development of Non-Insulin-Dependent Diabetes Mellitus and Related Abnormalities", J Diabetes Complications, Mar.-Apr. 1997; 11(2):69-76.
Harrison's Principles of Internal Medicine, Isselbacher et al. eds. McGraw-Hill, Inc., New York, 1994, p. 69.
Harrison's Principles of Internal Medicine, vol. 2, 23d ed., Ed by Isselbacher, Braunwald, Wilson, Martin, Fauci and Kasper, McGraw-Hill Inc New York City, 1994, p. 2275.
Hatzinger, M. et al., Wien. Med. Wochenschr. 1999, 149, 511-514.
Hauner H, "Managing type 2 diabetes mellitus in patients with obesity," Treatments in Endocrinology, 2004, 3(4), 223-232 (only abstract provided).
Headache Classification Committee of the International Headache Society. Cephalalgia 1988;8 Suppl 7:1-96.

(56) References Cited

OTHER PUBLICATIONS

Hering et al., "Sodium valproate in the treatment of cluster headache", Cephalalgia (Sep. 1989) 9(3) pp. 195-8.
Huisman, M. et al.: "Synthesis of N-(diemthylsulphamoyl)aldimines, a new type of aldimine derivative". Synthetic Communications, vol. 27, No. 6, 1997, pp. 945-952.
Jay et al., "Epilepsy, Migraine and EEG Abnormalities in Children: a Review & Hypothesis," Journal of Head and Face Pain, abstract, vol. 22, Issue 3, pp. 110-114, 1982.
Joffe, R.T. et al., Arch. Gen. Psychiatry 1993, 50, 397-393.
Johns Hopkins Clinical Trial of Topiramate for Cocaine Addiction (ClinicalTrials.gov), 2009.
Johnson, B A: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.
Johnson, SA CNS Drugs, 2005. vol. 19, No. 1 0, pp. 873-896.
Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.
Keck, P et al, "Valproate and carbamazepine in the treatment of panic and post traumatic stress disorders, withdrawals states . . . " J Clin Psychopharm, vol. 12, No. 1, p. 36S-41S, 1992.
Kent, J.M., Lancet 2000, 355, 911-918.
Ketter, T.A. et al., J. Olin. Psychiatry 1995, 56, 471-475.
Keung W.M. et al, "Daidzin and daidzein suppress free-choice ethanol intake by Syrian golden hamsters" Proc Natl Acad Sci, vol. 90, p. 1008-10012, Nov. 1993.
Klinger et al., "Inhibition of carbonic anhydrase-II by sulfamate and sulfamide groups: An investigation involving direct thermodynamic binding measurements" Journal of Medicinal Chemistry, vol. 49, No. 12, 15 Jun. 2006, pp. 3496-3500.
Kohno, H. et al.: "A Novel Synthesis of Isoquinolines Containing an Electron Withdrawing Substitute". Heterocycles, vol. 51, No. 1, 1999, pp. 103-117, XP008052600.
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan 1, 1996; p. 463-465.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Olin. Psychiatry 1998, 59, Suppl. 18, 10-17.
Malatynska et al., "Dominant-submissive behavior as models of mania and depression", Neuroscience and Biobehavioral Review, 29 (2005) 715-737.
Malatynska et al., "Submissive behavior in mice as a test for antidepressant drug activity", Neuroscience and Biobehavioral Review, 82 (2005) 306-313.
Maryanoff, B.E. et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1988, pp. 1315-1343.
Mathew, Ninan T., MD, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, November/December Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.
Meldrum B. et al., "Excitatory amino acid neurotoxicity and neurodegenerative disease" TIPS, vol. 11, 1990, pp. 379-387, XP000915223.
Moller, H.J. et al., Eur. Arch. Psychiatry Clin. Neurosci. 2000, 250, 57-68.
Moskowitz, M.A., "The Neurobiology of Vascular Head Pain", Annals of Neurology, vol. 16, Issue 2, pp. 157-168, 1984.
Mueller T I, "A double-blind, placebo-controlled pilot study of carbamazepine for the treatment of alcohol dependence", Alcoholism Clin Exp Res, vol. 21, No. 1, 1997, p. 86-92.
Mula et al., "The role of anticonvulsant drugs in anxiety disorders: a critical review of the evidence" Journal of Clinical Psychopharmacology, Williams and Wilkins, vol. 1.27, No. 3, 2007, pp. 263-272.
Myers, R.D., "New Drugs for the Treatment of Experimental Alcoholism", Alcohol, vol. 11, No. 6, 1994, p. 439-451.
Nemeroff, C.B., Depress. Anxiety 1996-1997, 4, 169-181.
Nickel et al., Journal of Affective Disorders, vol. 87(2-3), 2005, pp. 243-252.
Nies et al., Goodman & Gilman's The Pharmacological Basis of Therapeutics, 9th Edition, pp. 43-62, 1996.
Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).
Osborne et al, Abstract, Topiramate Improves Glycemic Control and Triglycerides in Animal Models 1 page The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.
Ottman et al., "Comorbidity of migraine and epilepsy", Neurology, 1994;44: 2105 (Abstract only).
Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, 1996, pp. 2859-2862 (2005).
Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.
Perry et al. "Sumatriptan: An Updated Review of its Use in Migraine", 1998, Drugs, vol. 55, No. 6, pp. 889-922.
Pini et al., "Anti-Epileptic Drugs in the Preventive Treatment of Migraine Headache: a Brief Review", (J. Headache Pain, 2001, 2:13-19.
Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.
Raguraman, et al., "Effects of topiramate in alcohol dependence [2]" Australian and New Zealand Journal of Psychiatry, 2005 Australia, vol. 39, No. 8, 2005, pp. 736-737.
Ramlo-Halsted BA, "The Natural History of Type 2 Diabetes", Primary Care Dec. 1999;26(4):771-89.
Reis et al. Craving decrease with topiramate in outpatient treatment for cocaine dependence: an open label trial, Rev Bras Psiquiatr 2008;30(2):132-5.
Rogaswki et al., Nature Medicine, vol. 10, No. 7, Jul. 2004, pp. 685-692.
Rogawski et al., Nature Reviews Neuroscience, vol. 5 (1), 2004, pp. 553-564.
Rouillon, F., Eur. Neuropsychopharmacol 1999, 9 Suppl. 3, S87-S92.
Rygula et al., "Anhedonia and motivational deficits in rats: Impact of chronic social stress", Behavioral Brain Research, 162 (2005) 127-134.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Shank et al., "Examination of two independent kinetic assays for determining the inhibition of carbonic anhydrases I and II: Structure-

(56) References Cited

OTHER PUBLICATIONS activity comparison of sulfamates and sulfamides" Chemical Biology and Drug Design, vol. 68, No. 2, 2006, pp. 113-119.
Sharma K, McCue P, Dunn Sr. Am J Physiol Renal Physiol. Jun. 2003;284(6):F1138-44.
Silberstein et al., "Migraine & Epilepsy", www.myepilepsy.com, 2002.
Sofuoglu et al., CNS Drugs 2005: 19(1), pp. 13-25.
Soledade et al.: "Toward the control of Leptosphaeria Maculans" Design, Synthesis, biological activity, and metabolism of potential detoxification inhibitors of the crucifer phytoalexin brassinin. Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Stoll et al., Harvard Rev. Psychiatry, Jul./Aug. 1996, vol. 4, No. 2, 77-89.
Storey et al, "Topiramate in Migraine Prevention: A Double Blind, Placebo-Controlled Study", 2001, Headache, 41, pp. 968-975.
Ten Have, R. et al.: "Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
Tenovuo, O. "Central Acetylcholinesterase Inhibitors in the Treatment of Chronic Traumatic Brain Injury-Clinical Experience in 111 Patients". Progress in Neuro-Psychopharmacology and Biological Psychiatry 2005 US, vol. 29, No. 1, Jan. 2005, pp. 61067. XP002431412.
The Merck Manual (1987), Merck Sharp & Dohme Research Laboratories, Rahway, NJ XP002144176, pp. 1351-1356.
The Merck Manual, 1999, Merck Research, Whitehouse Station, NJ XP002224345, Diabetes Mellitus, pp. 165-177.
Topiramate retrieved from STN Database Accession No. 1998:2562 XP002179444 Abstract & R&D Focus Drug News, Jul. 27, 1998.
Traube, W. et al.: "Zur Kenntnis des Sulfamids". Berichte der Deutschen Chemischen Gesellschaft, vol. 56, 1923, pp. 1656-1663, XP002393747.
Uhart et al., Addiction Biology, 14, pp. 43-64, 2008.
Uys et al., CNS Neurol Disord Drug Targets, 7(5), 2008, pp. 482-491.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Seggern, Randal L., et al, "Efficacy of Topiramate in Migraine Prophylaxis: A Retrospective Chart Analysis" Headache (2002), (42)804-809.
Waugh et al., "Topiramate: As Monotherapy in Newly Diagnosed Epilepsy" CNS Drugs, vol. 17, No. 13, 2003, pp. 985-992.
Wauquier a et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Weib, G. et al.: "Herstellung and Reaktionen von N-Monoalkylamidosulfonylchloriden" Liebigs Annalen Der Chemie, vol. 729, Dec. 1969, pp. 40-51, XP002187581.
Wheeler et al., "Topiramate-treated cluster headache", Neurology (Jul. 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainouse features in cluster headache", Headache (1998) 38/7 pp. 547-551.

Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
Winhusen et al. Drug and Alcohol Dependence 91 (207) 131-148, 2007.
Yang Y. et al., "Neuroprotection by delayed administration of topiratmate in rat model of middle cerebral artery embolization", Brain Research, vol. 804, No. 2, 1998, pp. 169-176, XP000921218.
York, DA et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.
Young, WB et al, "Topiramate: a case series study in migraine prophylaxis" Cephalalgia (2002), (22)659-663.
Ziegler. E., et al.: "Zur Reaktivitat von C=Ndoppelbindungssytemen, VI. Reaktionen mit Sulfonamiden and Sulfamiden". Zeitschrift Fur Naturforschung, vol. 30B, 1975, pp. 951-953, XP008067475.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508, 1982.
Kubicki et al., J Mol Struct., 2001, 531(1-3), p. 65-70.
Lee et al., Org. Chem 1990 55(25) pp. 6098-6104.
Muniz et al., SYNLETT, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Chemische Berichte 1959 92 pp. 509-513 (See English translation provided).
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, (2002), 12(2), pp. 217-242.
Supuran et al., Medicinal Research Reviews, vol. 23, No. 2, pp. 146-189, 2003.
Thakur at al., Bioorganic and Medicinal Chemistry, 12(2004), pp. 789-793.
Behl et al., Endocrinology, vol. 138, No. 1, pp. 101-106, 1997.
Coyle et al., Science, vol. 262, Issue 5134, pp. 689-695, 1993.
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
New England Journal of Medicine, vol. 342:505-507, 2001.
Merck Manuals Online Medical Library, www.merck.com, 2007.
Cleeves et al., "Trazodone is ineffective in essential tremor", J. Neurol Nerusurg Psychiatry, 1990, 53:268-269.
Koller et al., "Essential Tremor Variants: Effect of Treatment", abstract, Clinical Pharmacology, 1987.
Robinson et al. "Pregablin not Effective for Essential Tremor", www.medpagetoday.com, 2009.
Handley and Mithani, Naunyn. Schmied. Arch. Pharmacol., 327, 1-5, 1984.

(56) References Cited

OTHER PUBLICATIONS

Aron et al., Neuropharmacology, 10, 459-469, 1971.
Meert et al., Pharmacol. Biochem. Behav.; 2005, 80(2), pp. 309-326.
Byrn et al., Pharmaceutical Research, Kluwer Academic Publishers, New York, NY, US, vol. 12, No. 7, 1995, pp. 945-954.
Jones et al. "Screening for Major Depression in Epilepsy with Common Self-Report Depression Inventories", Epilepsia, May 2005; 46(5):731-735.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Harwood, AJ, Molecular Psychiatry (2005) 10,117-126.
Goodman and Gilman's The Pharmacological Basis of Therapeutics, Eleventh Edition, McGraw Hill, Hypnotics and Sedatives, Chapter 16, pp. 401-427 (2006).
Goodman and Gilman's The Pharmacological Basis of Therapeutics, Eleventh Edition, McGraw Hill, Hypnotics and Sedatives, Chapter 17, pp. 429-459 (2006).
Goodman and Gilman's The Pharmacological Basis of Therapeutics, Eleventh Edition, McGraw Hill, Hypnotics and Sedatives, Chapter 19, pp. 429-459 (2006).
MacDonald et al., CNS Drugs, 2002, 16(8): 549-562.
Walden et al., Neuropsychobiology, 1998,38: 181-84.
Swinyard et al., Antiepileptic Drugs, Third Edition, pp. 85-102, 1989.
Ca 835894-69-4 Sulfamide (1,3-benzodioxo1-2-ylmethyl) (2005).
CA PLUS 835894-63-8 Sulfamic acid (3,4-dihydro-2H-1-benzopyran-2-yl)methyl ester (2005).
CA PLUS 835894-65-0 Sulfamide [(3, 4-dihydro-2H-1-benzopyran-2-yl) methyl] (2005).
CA PLUS 835894-67-2 Sulfamic acid (1,3-benzodioxo1-2-ylmethyl ester) (2005).
Notice of Allowance dated Mar. 20, 2012 in U.S. Appl. No. 11/209,122.
Notice of Allowance dated Jan. 17, 2012 in U.S. Appl. No. 11/406,794.
Notice of Allowance dated May 10, 2012 in U.S. Appl. No. 11/406,794.
Notice of Allowance dated Feb. 6, 2012 in U.S. Appl. No. 11/611,961.
Notice of Allowance dated May 23, 2012 in U.S. Appl. No. 11/611,961.
Notice of Allowance mailed Apr. 25, 2012 in U.S. Appl. No. 11/612,146.
Interview Summary mailed Mar. 26, 2012 in U.S. Appl. No. 12/431,141.
Notice of Allowance mailed Apr. 16, 2012 in U.S. Appl. No. 11/612,202.
Notice of Allowance dated May 11, 2012 in U.S. Appl. No. 13/301,109.
Office Action mailed Mar. 30, 2012 in U.S. Appl. No. 11/750,600.
Interview Summary mailed Apr. 4, 2012 in U.S. Appl. No. 12/055,433.
Notice of Allowance dated May 11, 2012 in U.S. Appl. No. 12/349,184.
Notice of Allowance mailed Mar. 1, 2012 in U.S. Appl. No. 12/488,079.
Notice of Allowance mailed Mar. 28, 2012 in U.S. Appl. No. 12/502,472.
Brodie, M.S.; Pesold, C; Appel, S.B. Alcohol Clin Exp Res 1999, 23, pp. 1848-1852.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, AM., (2006) Epilepsy, suicidal behaviour, and depression: do they share common pathogenic mechanisms? Lancet Neurol 5:107-108.
Krampfl et al., The European Journal of Neuroscience; vol. 22, Issue: 1, pp. 10-20, 2005.
Ottman et al., Epilepsia, 52(2):308-315, 2011.
Scimemi et al., The Journal of Neuroscience: the official journal of Society for Neuroscience; vol. 25; Issue: 43, pp. 10016-10024, 2005.
Sullivan, P., Epilepsy & Behavior 7 (2005) S12-S17.
Wise RA, Drug Alcohol Depend, 1998, 51, pp. 13-22.
Wise RA, NIDA Res Mono, 1984,50, pp. 15-33.
Notice of Allowance dated Jul. 19, 2012 in U.S. Appl. No. 11/154,386.
Notice of Allowance dated Nov. 20, 2012 in U.S. Appl. No. 11/154,386.
Notice of Allowance mailed Dec. 24, 2012 in U.S. Appl. No. 11/611,938.
Notice of Allowance dated Aug. 27, 2012 in U.S. Appl. No. 11/611,961.
Notice of Allowance dated Dec. 10, 2012 in U.S. Appl. No. 11/611,961.
Notice of Allowance mailed Jan. 4, 2012 in U.S. Appl. No. 11/612,202.
Notice of Allowance mailed Aug. 9, 2012 in U.S. Appl. No. 11/612,202.
Notice of Allowance mailed Nov. 26, 2012 in U.S. Appl. No. 11/612,202.
Final Office Action mailed Sep. 10, 2012 in U.S. Appl. No. 11/750,600.
Office Action mailed Mar. 14, 2013 in U.S. Appl. No. 11/750,600.
Notice of Allowance mailed Jun. 18, 2012 in U.S. Appl. No. 12/488,079.
Notice of Allowance mailed Oct. 10, 2012 in U.S. Appl. No. 12/488,079.
Notice of Allowance mailed Feb. 7, 2013 in U.S. Appl. No. 12/488,079.
Notice of Allowance mailed Jul. 16, 2012 in U.S. Appl. No. 12/502,472.
Benjamin et al. J Biomol Screening, 2006, vol. 11, pp. 29-39.
Brandt et al., Neuropsychobiology, 1998, 38, pp. 202 to 203.
Brown et al. Tetrahedron, 1987, vol. 43, pp. 4071-4078.
Dib, Jean G., Current Medical Research and Opinion, 2004, 20, 12, p. 1857-1861.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp. 737-748.
Keck et al., J. Clin. Psychiatry, 2002, 63 (suppl 4).

(56) References Cited

OTHER PUBLICATIONS

Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Remington's The Science and Practice of Pharmacy, $19^{th}$ Edition, Published 1998, vol. I, pp. 371-375.
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym Inh Med Chem, 2008, vol. 23, pp. 271-276.
Shingles et al., Anal Biochem, 1997, vol. 252, pp. 190-197.
Soderpalm, B., Eur J Pain, 2002, vol. 6, Suppl A, p. 3-9.
Stella et al., Drugs, 29: 455-473 (1985).
Swinyard et al., J Pharmacol Exp Ther, 1952, vol. 106, pp. 319-330.
Swinyard, E., Epilepsia, 1969, vol. 10, pp. 107-119.
Tanimukai et al., International Pharmacopsychiatry, 1970, vol. 5, No. 1, pp. 35 to 43.
Thienel et al., Acta Neurologica Scandinavica, 2004, 110, 4, p. 221-231.
Wang et al., Science, 1998 vol. 282, pp. 1890-1893.
White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.
Notice of Allowance dated May 8, 2013 in U.S. Appl. No. 11/154,386.
Notice of Allowance dated Aug. 29, 2013 in U.S. Appl. No. 11/154,386.
Notice of Allowance dated May 10, 2013 in U.S. Appl. No. 11/209,122.
Notice of Allowance dated Sep. 16, 2013 in U.S. Appl. No. 11/209,122.
Notice of Allowance mailed Mar. 27, 2013 in U.S. Appl. No. 11/611,938.
Notice of Allowance dated Apr. 2, 2013 in U.S. Appl. No. 11/611,961.
Notice of Allowance mailed Sep. 23, 2013 in U.S. Appl. No. 11/612,146.
Office Action mailed Jul. 19, 2013 in U.S. Appl. No. 12/431,141.
Notice of Allowance mailed Mar. 18, 2013 in U.S. Appl. No. 11/612,202.
Notice of Allowance mailed Jul. 9, 2013 in U.S. Appl. No. 11/612,202.
Office Action mailed Aug. 6, 2013 in U.S. Appl. No. 11/612,222.
Final Office Action mailed Aug. 13, 2013 in U.S. Appl. No. 11/750,600.
Office Action mailed May 23, 2013 in U.S. Appl. No. 12/055,433.
Notice of Allowance mailed Mar. 27, 2013 in U.S. Appl. No. 12/488,079.
Notice of Allowance mailed Aug. 9, 2013 in U.S. Appl. No. 12/488,079.
Notice of Allowance mailed Apr. 29, 2013 in U.S. Appl. No. 12/502,472.
Loscher et al. Antiepileptogenic effects of the novel anticonvulsant levetiracetam (ucb L059) in the kindling model of temporal lobe epilepsy. The Journal of Pharmacology and Experimental Therapeutics, vol. 284, No. 2, 1998, pp. 474-479.
Loscher, et al., Pharma. Rev., 62, 668-700 (2010).
McNamara et al. Analyses of the molecular basis of kindling development. Psychiatry and Clinical Neurosciences, 1995, 49, S175-S178.
Walker, et al., Brain, 125, 1937-1950 (2002).

\* cited by examiner

USE OF BENZO-FUSED HETEROCYCLE SULFAMIDE DERIVATIVES FOR THE TREATMENT OF PAIN

CROSS REFERENCE TO RELATED APPLICATIONS

This application claims the benefit of U. S. Provisional Application 60/751,686, filed on Dec. 19, 2005, and U.S. Provisional Application 60/773,812, filed on Feb. 15, 2006, which are incorporated by reference herein in their entirety.

FIELD OF THE INVENTION

The present invention is directed to the use of benzo-fused heterocycle sulfamide derivatives for the treatment of acute, chronic, inflammatory and/or neuropathic pain.

BACKGROUND OF THE INVENTION

Pain is generally defined as an unpleasant sensory and emotional experience, associated with actual or potential tissue damage (Wileman L, Advances in pain management, *Scrip Report*, 2000).

Acute pain is a physiological response to an adverse chemical, thermal or mechanical stimulus that may be associated with surgery, trauma or acute illness. These conditions include, but are not limited to, post-operative pain, sports medicine injuries, carpal tunnel syndrome, burns, musculoskeletal sprains and strains, musculotendinous strain, cervicobrachial pain syndromes, dyspepsia, gastric ulcer, duodenal ulcer, kidney stone pain, gallbladder pain, gallstone pain, dysmenorrhea, endometriosis, obstetric pain, rheumatological pain, headache or dental pain.

Chronic pain is a pain condition beyond the normal cause of an injury or illness and may be a consequence of inflammation or serious, progressive, painful disease stages. Various types of chronic pain include, but are not limited to, headache, migraine, trigeminal neuralgia, temporomandibular joint syndrome, fibromyalgia syndrome, osteoarthritis, rheumatoid arthritis, bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy)), pelvic pain, cardiac chest pain, non-cardiac chest pain, spinal cord injury-associated pain, central post-stroke pain, cancer pain, AIDS pain, sickle cell pain or geriatric pain.

Neuropathic pain is defined as pain caused by aberrant somatosensory processing in the peripheral or central nervous system and includes painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome and other chronic and debilitating condition-associated pain syndromes.

There remains a need to provide an effective treatment for pain.

SUMMARY OF THE INVENTION

The present invention is directed to a method for the treatment of pain comprising administering to a subject in need thereof a therapeutically effective amount of a compound of formula (I)

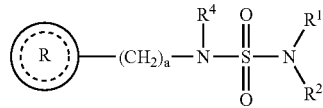

wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

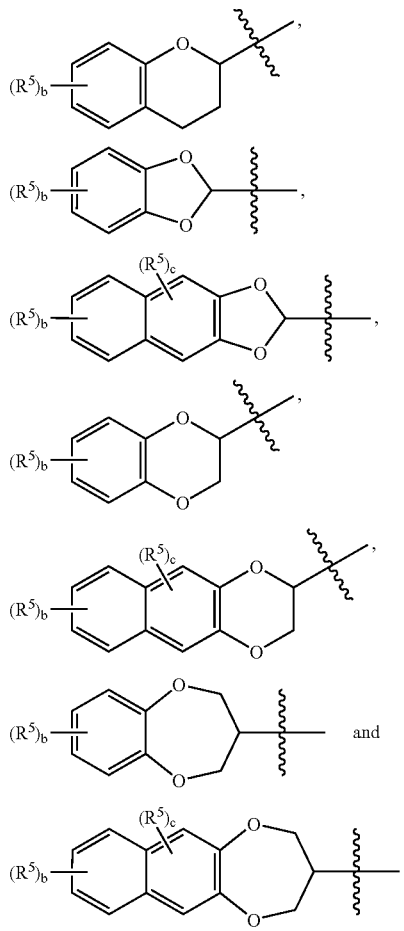

wherein b is an integer from 0 to 4; and wherein c is an integer from 0 to 2;

each $R^5$ is independently selected from the group consisting of halogen, lower alkyl and nitro;

provided that when

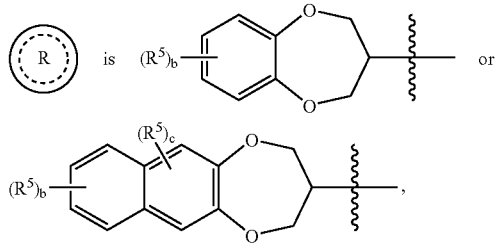

then a is 1;
or a pharmaceutically acceptable salt thereof.

The present invention is further directed to a method for the treatment of pain comprising administering to a subject in need thereof a therapeutically effective amount of compound of formula (II)

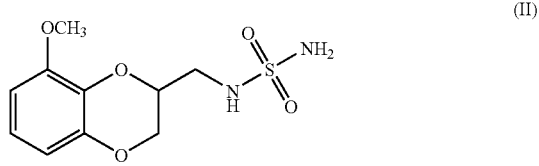

(II)

or a pharmaceutically acceptable salt thereof.

Exemplifying the invention is a method of treating pain, wherein the pain is selected from the group consisting of acute pain or chronic pain, comprising administering to a subject in need thereof a therapeutically effective amount of any of the compounds or pharmaceutical compositions described above.

Further exemplifying the invention is a method of treating pain, wherein the pain is inflammatory pain, comprising administering to a subject in need thereof a therapeutically effective amount of any of the compounds or pharmaceutical compositions described above.

Further exemplifying the invention is a method of treating pain, wherein the pain is neuropathic pain, comprising administering to a subject in need thereof a therapeutically effective amount of any of the compounds or pharmaceutical compositions described above.

The present invention is further directed to methods for the treatment of pain comprising administering to a subject in need thereof, co-therapy with at least one analgesic agent and a compound of formula (I) or formula (II) as described herein.

DETAILED DESCRIPTION OF THE INVENTION

The present invention is directed to a method for the treatment of pain comprising administering to a subject in need thereof a therapeutically effective amount of a compound of formula (I)

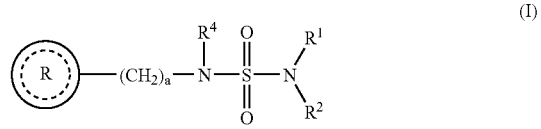

(I)

or a pharmaceutically acceptable salt thereof, wherein

a, $R^1$, $R^2$ and $R^4$ are as herein defined. The present invention is further directed to methods of treating pain comprising co-therapy with a least on analgesic agent and a compound of formula (I) or formula (II) as described herein.

As used herein, the term "pain" shall be defined to include acute, chronic, inflammatory and neuropathic pain (preferably diabetic neuropathy). Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

In an embodiment of the present invention, is a method for the treatment of pain, wherein the pain is acute pain. In another embodiment of the present invention, is a method for the treatment of pain, wherein the pain is chronic pain. In another embodiment of the present invention, is a method for the treatment of pain, wherein the pain is neurpoathic pain, more preferably diabetic neuropathy. In yet another embodiment of the present invention, is a method for the treatment of pain, wherein the pain is inflammatory pain.

In an embodiment, the pain is selected from the group consisting of osteoarthritis, rheumatoid arthritis, fibromyalgia, headache, toothache, burn, sunburn, animal bite (such as dog bite, cat bite, snake bite, spider bite, insect sting, and the like), neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, labor, childbirth, menstrual cramps, cancer, back pain, lower back pain and carpal tunnel syndrome pain.

Acute pain includes pain caused by acute injury, trauma, illness or surgery (for example, open-chest surgery (including open-heart or bypass surgery)). Acute pain also includes, and is not limited to, headache, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, headache, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

Neuropathic pain includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes.

As used herein, the term "analgesic agent" shall mean any pharmaceutical agent which provide alleviation of pain, including, but not limited to opiods and derivative thereof, non-steroidal anti-inflammatory agents, Tylenol-like compounds, NO donating compounds, TRAMADOL and TRAMADOL-like compounds and antidepressants such as amitriptyline. Preferably, the analgesic-agent is TRAMADOL or Tylenol.

Suitable examples include, but are not limited to Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium and Zucapsaicin.

Additionally, the analgesic may be combination product, including, but not limited Novartis' FIORICET or Forests' ESGIC or generics (combination of acetaminophen and butalbital and caffeine), FIORINAL or generics (combination of aspirin, butalbital and caffeine, Novartis), MIGPRIV or generics (combination of aspirin and metoclopromide; Sanofi-Synthelabo), MIDRIN/MIDRID or generics (combination of acetaminophen and dichloralphenazone; Carnick), Sanofi-Synthelabo's PARAMAX or Dolorgiet's MIGRAEN-ERTON or generics (combination of paracetamol and metoclopramide), Abbott's VICODIN or generics (combination of acetaminophen and hydrocodone), STADOL NS (butorphanol nasal spray; Bristol-Myers Squibb), Boehringer Ingelheim's LONARID or Pfizer's MIGRALEVE or generics (combination of paracetamol and codeine), and the like.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of one or more compound(s) of formula (I) or formula (II) and one or more analgesic agents, "therapeutically effective amount" shall mean that amount of the combination of agents taken together so that the combined effect elicits the desired biological or medicinal response. For example, the therapeutically effective amount of co-therapy comprising administration of a compound of formula (I) or formula (II) and at least on analgesic agent would be the amount of the compound of formula (I) or formula (II) and the amount of the analgesic agent that when taken together or sequentially have a combined effect that is therapeutically effective. Further, it will be recognized by one skilled in the art that in the case of co-therapy with a therapeutically effective amount, as in the example above, the amount of the compound of formula (I) or formula (II) and/or the amount of the analgesic agent individually may or may not be therapeutically effective.

As used herein, the terms "co-therapy" and "combination therapy" shall mean treatment of a subject in need thereof by administering one or more compounds of formula (I) or formula (II) in combination with one or more analgesic agent(s), wherein the compound(s) of formula (I) or formula (II) and the analgesic agent(s) are administered by any suitable means, simultaneously, sequentially, separately or in a single pharmaceutical formulation. Where the compound(s) of formula (I) or formula (II) and the analgesic agent(s) are administered in separate dosage forms, the number of dosages administered per day for each compound may be the same or different. The compound(s) of formula (I) or formula (II) and the analgesic agent(s) may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intra-vertebral needles and/or catheters with or without pump devices. The compound(s) of formula (I) or formula (II) and the analgesic agent(s) may be administered according to simultaneous or alternating regimens, at the same or different times during the course of the therapy, concurrently in divided or single forms.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —$(CH_2)_a$— is selected from the group consisting of —$CH_2$— and —$CH_2$—$CH_2$—. In another embodiment of the present invention —$(CH_2)_a$— is —$CH_2$—.

In an embodiment of the present $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is selected from the group consisting of

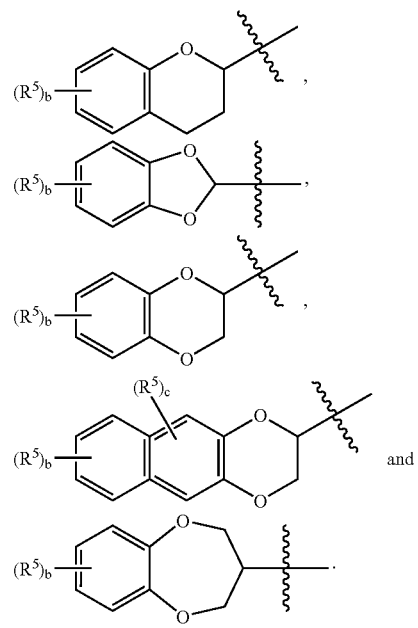

In another embodiment of the present invention, is selected from the group consisting of

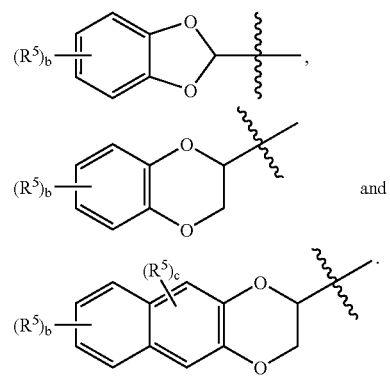

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention,

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In an embodiment of the present invention $R^5$ is selected from the group consisting of halogen and lower alkyl. In another embodiment of the present invention $R^5$ is selected from chloro, fluoro, bromo and methyl.

In an embodiment of the present invention, the stereo-center on the compound of formula (I) is in the S-configuration. In another embodiment of the present invention, the stereo-center on the compound of formula (I) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

Additional embodiments of the present invention, include those wherein the substituents selected for one or more of the variables defined herein (i.e. $R^1$, $R^2$, $R^3$, $R^4$, X—Y and A) are independently selected to be any individual substituent or any subset of substituents selected from the complete list as defined herein.

Representative compounds of the present invention, are as listed in Tables 1 below. Additional compounds of the present invention are as listed in Table 3. In Tables 1 and 2 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | $(CH_2)_a$ | $NR^4$ | $R^1$ | $R^2$ |
|---|---|---|---|---|---|---|
| 1 | 2-(3-dihydro-benzo[1,4]dioxinyl) | | $CH_2$ | NH | H | H |
| 2 | 2-(benzo[1,3]dioxolyl) | | $CH_2$ | NH | H | H |
| 3 | 3-(3,4-dihydro-2H-benzo[1,4]dioxepinyl) | | $CH_2$ | NH | H | H |
| 4 | 2-(2,3-dihydro-benzo[1,4]dioxinyl) | S | $CH_2$ | NH | H | H |
| 5 | 2-(2,3-dihydro-benzo[1,4]dioxinyl) | R | $CH_2$ | NH | H | H |
| 6 | 2-(2,3-dihydro-benzo[1,4]dioxinyl) | | $CH_2$ | NH | mthyl | methyl |
| 7 | 2-(2,3-dihydro-benzo[1,4]dioxinyl) | | $CH_2$ | $N(CH_3)$ | H | H |
| 8 | 2-(6-chloro-2,3-dihydro-benzo[1,4]dioxinyl) | S | $CH_2$ | NH | H | H |
| 9 | 2-(6-fluoro-2,3-dihydro-benzo[1,4]dioxinyl) | S | $CH_2$ | NH | H | H |
| 10 | 2-(chromanyl) | | $CH_2$ | NH | H | H |
| 13 | 2-(5-fluoro-2,3-dihydro-benzo[1,4]dioxinyl) | S | $CH_2$ | NH | H | H |
| 14 | 2-(7-chloro-2,3-dihydro-benzo[1,4]dioxinyl) | S | $CH_2$ | NH | H | H |
| 15 | 2-(6-chloro-benzo[1,3]dioxolyl) | | $CH_2$ | NH | H | H |
| 16 | 2-(2,3-dihydro-benzo[1,4]dioxinyl) | | $CH_2CH_2$ | NH | H | H |
| 18 | 2-(7-nitro-2,3-dihydro-benzo[1,4]dioxinyl) | S | $CH_2$ | NH | H | H |
| 19 | 2-(7-methyl-2,3-dihydro-benzo[1,4]dioxinyl) | S | $CH_2$ | NH | H | H |
| 20 | 2-(5-chloro-2,3-dihydro-benzo[1,4]dioxinyl) | S | $CH_2$ | NH | H | H |

TABLE 1-continued

Representative Compounds of Formula (I)

$$\text{(R)}*-(CH_2)_a-N(R^4)-S(=O)_2-N(R^1)(R^2)$$

| ID No. | (R) | Stereo | $(CH_2)_a$ | $NR^4$ | $R^1$ | $R^2$ |
|---|---|---|---|---|---|---|
| 22 | 2-(8-meethoxy-2,3-dihydro-benzo[1,4]dioxinyl) | S | $CH_2$ | NH | H | H |
| 24 | 2-(6-bromo-2,3-dihydro-benzo[1,4]dioxinyl) | S | $CH_2$ | NH | H | H |
| 29 | 2-(6,7-dichloro-2,3-dihydro-benzo[1,4]ddioxinyl) | S | $CH_2$ | NH | H | H |
| 30 | 2-(8-chloro-2,3-dihydro-benzo[1,4]dioxinyl) | S | $CH_2$ | NH | H | H |
| 31 | 2-(2,3-dihydro-naphtho[2,3-b][1,4]dioxinyl) | S | $CH_2$ | NH | H | H |
| 35 | 2-(4-methyl-benzo[1,3]dioxiolyl) | | $CH_2$ | NH | H | H |

TABLE 2

Additional Compounds of the Present Invention $$\text{(Y)}*-X-N(R^{14})-S(=O)_2-N(R^{11})(R^{12})$$

| ID No. | (Y) | Stereo | X | $NR^{14}$ | $R^{11}$ | $R^{12}$ |
|---|---|---|---|---|---|---|
| 23 | 2-(5-methoxy-2,3-dihydro-benzo[1,4]dioxinyl) | S | $CH_2$ | NH | H | H |
| 26 | 2-(6-methylcarbonyl-2,3-dihydro-benzo[1,4]dioxinyl) | S | $CH_2$ | NH | H | H |
| 32 | 2-(6-methoxycarbonyl-2,3-dihydro-benzo[1,4]ddioxinyl) | S | $CH_2$ | NH | H | H |
| 34 | 2-(6-hydroxymethyl-2,3-dihydro-benzo[1,4]dioxinyl) | S | $CH_2$ | NH | H | H |
| 36 | 2-(7-amino-2,3-dihydro-benzo[1,4]dioxinyl) | S | $CH_2$ | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, prefer- ably from one to five substituents, more preferably from one to three substituents, most preferably from one to two sub- stituents, independently selected from the list of substituents.

With reference to substituents, the term "independently" means that when more than one of such substituents is pos- sible, such substituents may be the same or different from each other.

Under standard nomenclature used throughout this disclo- sure, the terminal portion of the designated side chain is described first, followed by the adjacent functionality toward the point of attachment. Thus, for example, a "phenyl-alkyl- amino-carbonyl-alkyl" substituent refers to a group of the formula

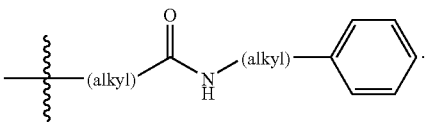

Abbreviations used in the specification, particularly the Schemes and Examples, are as follows:
DCC=Dicyclohexyl Carbodiimide
DCE=Dichloroethane
DCM=Dichloromethane
DIPEA or DIEA=Diisopropylethylamine
DMF=N,N-Dimethylformamide
DMSO=Dimethylsulfoxide
EDC=Ethylcarbodiimide
Et3N or TEA=Triethylamine
Et$_2$O=Diethyl ether
EA or EtOAc=Ethyl acetate
EtOH=Ethanol
IPA=2-propanol
Hept=Heptane
HOBT=1-Hydroxybenzotriazole
HPLC=High Pressure Liquid Chromatography
LAH=Lithium Aluminum Hydride
M or MeOH=Methanol
NMR=Nuclear Magnetic Resonance Pd-C=Palladium on Carbon Catalyst
RP HPLC=Reverse Phase High Pressure Liquid Chromatography
RT or rt=Room temperature
TEA=Triethylamine
TFA=Trifluoroacetic Acid
THF=Tetrahydrofuran
TLC=Thin Layer Chromatography Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

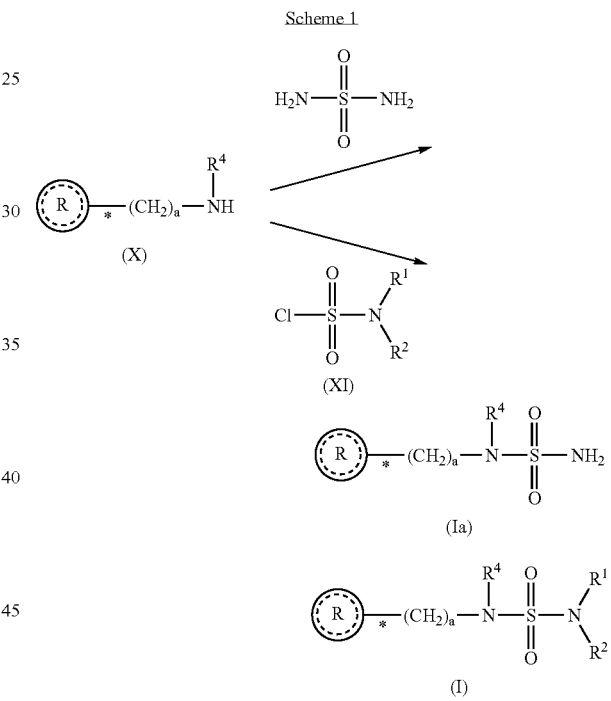

Accordingly, a suitably substituted compound of formula (X), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (Ia).

Alternatively, a suitably substituted compound of formula (X), a known compound or compound prepared by known methods, is reacted with a suitably substituted compound of formula (XI), a known compound or compound prepared by known methods, in the presence of a base such as TEA, DIPEA, pyridine, and the like, in an organic solvent such as DMF, DMSO, and the like, to yield the corresponding compound of formula (I).

Compounds of formula (X) wherein

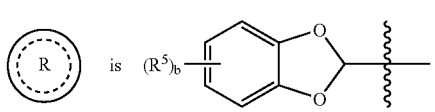

may be prepared according to the process outlined in Scheme 2.

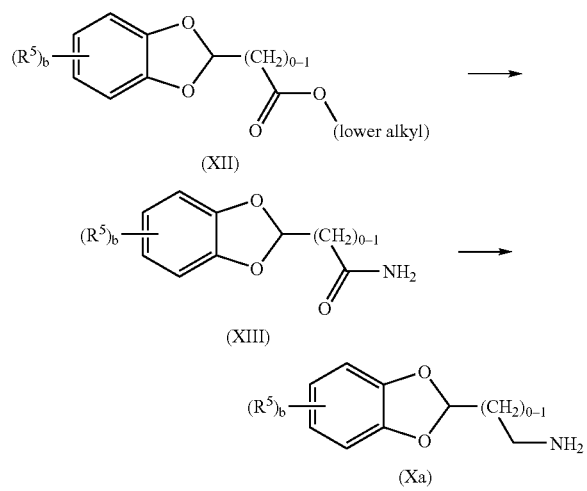

Accordingly, a suitably substituted compound of formula (XII), a known compound or compound prepared by known method (for example as described in Scheme 3 above) is reacted with NH₄OH, a known compound, optionally in an organic solvent such as acetonitrile, and the like, to yield the corresponding compound of formula (XIII).

The compound of formula (XIII) is reacted with a suitably selected reducing agent, such as LAH, and the like, and the like, in an organic solvent such as THF, diethyl ether, and the like, to yield the corresponding compound of formula (Xa).

Compounds of formula (X) wherein

is selected from

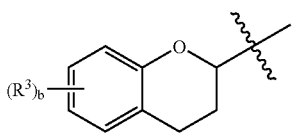

may be prepared according to the process outlined in Scheme 3.

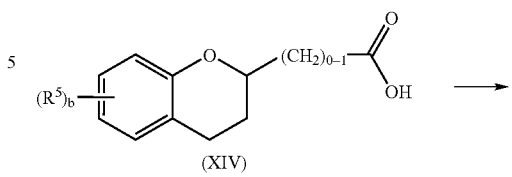

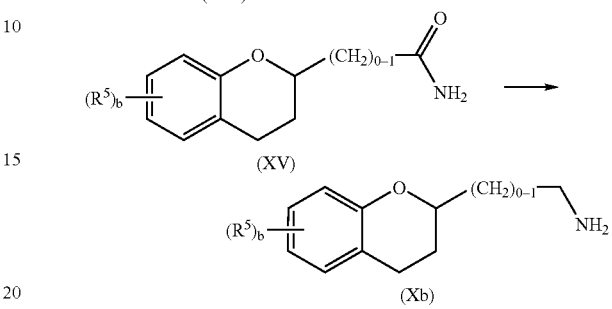

Accordingly, a suitably substituted compound of formula (XIV), a known compound or compound prepared by known methods, is reacted with NH₄OH, in the presence of a coupling agent such as DCC, and the like, optionally in an organic solvent such as acetonitrile, and the like, to yield the corresponding compound of formula (XV).

The compound of formula (XV) is reacted with a suitably selected reducing agent, such as LAH, and the like, in an organic solvent such as THF, diethyl ether, and the like, to yield the corresponding compound of formula (Xb).

Compounds of formula (X) wherein

is selected from

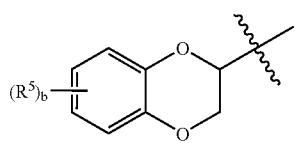

and wherein a is 2, may be prepared according to the process outlined in Scheme 4.

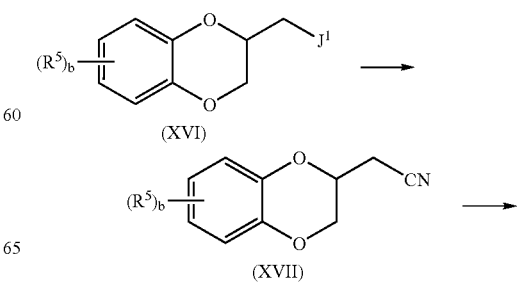

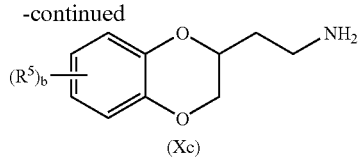

(Xc)

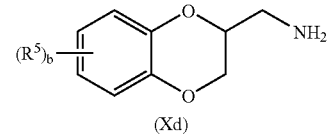

(Xd)

Accordingly, a suitably substituted compound of formula (XVI) wherein $J^1$ is a suitable leaving group such as Br, Cl, I, tosyl, mesyl, triflyl, and the like, a known compound or compound prepared by known methods (for example, by activating the corresponding compound wherein $J^1$ is OH), is reacted with a cyanide such as potassium cyanide, sodium cyanide, and the like, in an organic solvent such as DMSO, DMF, THF, and the like, to yield the corresponding compound of formula (XVII).

The compound of formula (XVII) is reduced according to known methods, for example by reacting with a suitable reducing agent such as LAH, borane, and the like, to yield the corresponding compound of formula (Xc).

Compounds of formula (X) wherein

is selected from

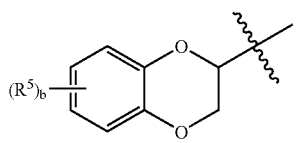

and wherein a is 1, may be prepared according to the process outlined in Scheme 5.

Accordingly, a suitably substituted compound of formula (XVIII), a known compound or compound prepared by known methods is activated, according to known method, to yield the corresponding compound of formula (XIX), wherein $J^2$ is a suitable leaving group, such tosylate, Cl, Br, I, mesylate, triflate, and the like.

The compound of formula (XIX) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XX).

The compound of formula (XX) is reacted with $N_2H_4$, a known compound, in an organic solvent such as ethanol, methanol, and the like, preferably at an elevated temperature in the range of from about 50° C. to about 100° C., more preferably, at about reflux temperature, and the like, to yield the corresponding compound of formula (Xd).

One skilled in the art will recognize that compounds of formula (X) wherein

is selected from

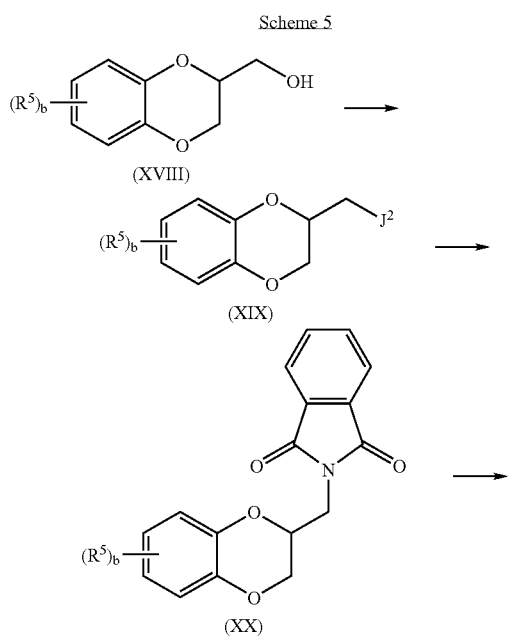

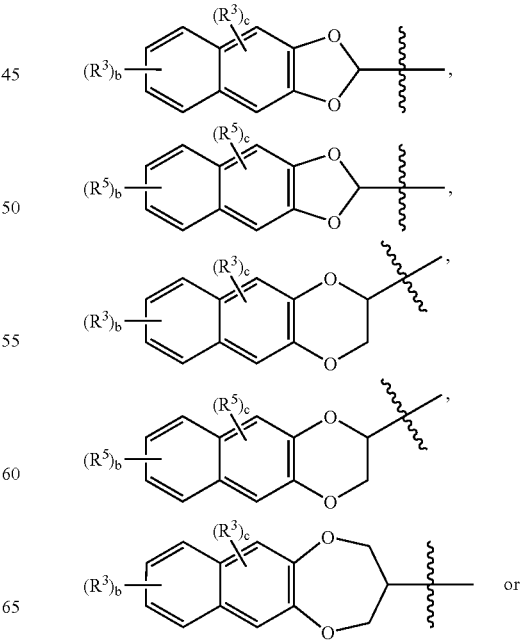

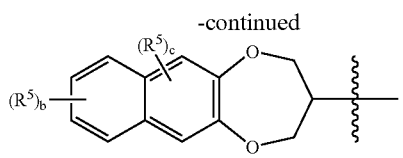

may be similarly prepared according to known methods or for example, according to the processes outlined in Schemes 2 through 5 above, by selecting and substituting the corresponding naphthyl-fused compounds for the benzo-fused starting materials.

One skilled in the art will further recognize that wherein a single enantiomer (or a mixture of enantiomers wherein one enantiomer is enriched) of a compound of formula (X) is desired, the above processes as described in Schemes 1 through 5 may be applied by substituting the corresponding single enantiomer (or mixture of enantiomers wherein one enantiomer is enriched) for the appropriate starting material.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desiredroute of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.01-200.0 mg/kg/day, preferably from about 0.1 to 100 mg/kg/day, more preferably from about 0.5-50 mg/kg/day, more preferably from about 1.0-25.0 mg/kg/day or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating depression described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of depression is required.

The daily dosage of the products may be varied over a wide range from 0.01 to 200 mg/kg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

EXAMPLE 1

((3,4-Dihydro-2H-benzo[b][1,4]dioxepin-3-yl)methyl)sulfamide (Compound #3)

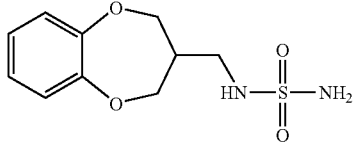 [SMILES: NS(=O)(=O)NCC1COc2ccccc2OC1]

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over MgSO$_4$ and concentrated. Chromatography (2% ethyl ether in hexane) yielded 3-methylene-3,4-dihydro-2H-benzo[b][1,4]dioxepine as a colorless oil.

MS (ESI): 163.2 (M+H$^+$)

$^1$H NMR (300 MHz, CDCl$_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over MgSO$_4$. The solution was concentrated under vacuum and purified by chromatography (2% to 8% methanol in dichloromethane) to yield ((3,4-dihydro-2H-benzo[b][1,4]dioxepin-3-yl)methyl) amine as a colorless oil.

MS (ESI): 180.1 (M+H$^+$)

$^1$H NMR (300 MHz, DMSO), δ: 6.92 (m, 4H), 4.21 (m, 2H), 4.07 (m, 2H), 3.33 (broad, 2H), 3.16 (d, J=4 Hz, 1H), 2.72 (d, J=4 Hz, 1H), 2.30 (m, 1H).

((3,4-Dihydro-2H-benzo[b][1,4]dioxepin-3-yl)methyl) amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 (M+H$^+$)

$^1$H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

EXAMPLE 2

N-(2,3-Dihydro-benzo[1,4]dioxin-2-ylmethyl)-sulfamide (Compound #1)

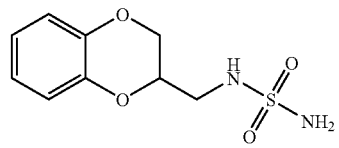 [SMILES: NS(=O)(=O)NCC1COc2ccccc2O1]

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol-10:1) to yield a white solid. The solid was recrystallized from DCM to yield the title compound as a white solid.

mp: 97.5-98.5° C.

Elemental Analysis:

Anal Calc: C, 44.25; H, 4.95; N, 11.47; S, 13.13

Anal Found: C, 44.28; H, 4.66; N, 11.21; S, 13.15

H$^1$ NMR (DMSO d6) δ 6.85 (m, 4H), 6.68 (bd s, 3H, NH), 4.28 (m, 2H), 3.97 (dd, J=6.9, 11.4 Hz, 1H), 3.20 (m, 1H), 3.10 (m, 1H).

EXAMPLE 3

(Benzo[1,3]dioxol-2-ylmethyl)sulfamide (Compound #2)

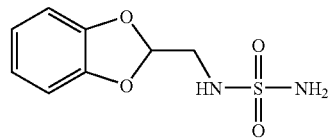 [SMILES: NS(=O)(=O)NCC1Oc2ccccc2O1]

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with MgSO$_4$, concentrated to a brown solid, and chromatographed (2% ethyl acetate in hexane) to yield benzo[1,3]dioxole-2-carboxylic acid methyl ester as a colorless oil.

MS (ESI): 195.10 (M+H$^+$)

$^1$H NMR (300 MHz, CDCl$_3$), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added. Benzo[1,3]dioxole-2-carboxylic acid amide precipitated as a white solid and was collected by filtration and used without further purification.

MS (ESI): 160.00 (M+H$^+$)

$^1$H NMR (300 MHz, DMSO, δ: 7.99 (s, broad, 1H), 7.72 (s, broad, 1H), 6.94 (m, 2H) 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over MgSO$_4$. The solvent was evaporated to yield C-benzo[1,3]dioxol-2-yl-methylamine as a colorless oil.

MS (ESI): 152.1 (M+H$^+$)

$^1$H NMR (300 MHz, CDCl$_3$), δ: 6.87 (m, 4H), 6.09 (t, J=4 Hz, 1H), 3.13 (d, J=4 Hz, 2H)

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 (M+H$^+$)

$^1$H NMR (300 MHz, CDCl$_3$), δ: 6.87 (m, 4H), 6.25 (t, J=4 Hz, 1H), 4.79 (broad, 1H), 4.62 (broad, 1H), 3.64 (d, J=4 Hz, 2H).

EXAMPLE 4

(2S)-(−)-N-(2,3-Dihydro-benzo[1,4]dioxin-2-ylmethyl)-sulfamide (Compound #4)

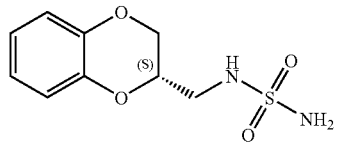

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1L) and 1 N HCl (1.2L). The organic layer was separated and washed 2 times with 1 N HCl (500 mL), 4 times with water (150 mL), once with brine, dried (MgSO$_4$) and evaporated in vacuo to yield a white solid which was purified by flash column chromatography (Hept:EA—2:1) to yield toluene-4-sulfonic acid (2S)-2,3-dihydro-benzo[1,4]dioxin-2-ylmethyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)—C-(2,3-Dihydro-benzo[1,4] dioxin-2-yl)-methylamine) was filtered off and then recrystallized again from 2-propanol to yield a white solid.

[α]$_D$=−69.6 (c=1.06, EtOH)

The white solid was partitioned between DCM and dilute NaOH, and the DCM was dried (NaSO$_4$) and evaporated in vacuo to yield (2S)—C-(2,3-Dihydro-benzo[1,4]dioxin-2-yl)-methylamine as an oil.

[α]$_D$=57.8 (c=1.40, CHCl$_3$)

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C.

[α]$_D$=45.1° C.(c=1.05, M);

$^1$H NMR (DMSOd6) δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H)

Elemental Analysis:
Anal Calc: C, 44.25; H, 4.95; N, 11.47; S, 13.13
Anal Found: C, 44.20; H, 4.69; N, 11.40; S, 13.22.

EXAMPLE 5

N-(2,3-Dihydro-benzo[1,4]dioxin-2-ylmethyl)-N', N'dimethylsulfamide (Compound #6)

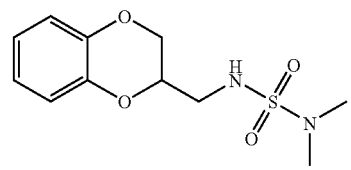 [SMILES: CN(C)S(=O)(=O)NCC1COc2ccccc2O1]

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried (MgSO$_4$) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C.

MS 273 (MH$^+$)

Elemental Analysis:

Anal Calc: C, 48.52; H, 5.92; N, 10.29; S, 11.78

Anal Found: C, 48.63; H, 5.62; N, 10.20; S, 11.90

$^1$H NMR (CDCl$_3$) δ 6.87 (m, 4H), 4.59 (bd m, 1 H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

EXAMPLE 6

N-(2,3-Dihydro-benzo[1,4]dioxin-2-ylmethyl)-N-methylsulfamide (Compound #7)

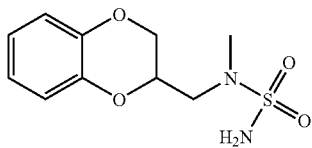 [SMILES: CN(CC1COc2ccccc2O1)S(N)(=O)=O]

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1 M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried (MgSO$_4$) and evaporated in vacuo to yield (2,3-dihydro-benzo[1,4]dioxin-2-ylmethyl)-methyl-amine as an oil.

MS 180 (MH$^+$)

$^1$H NMR (CDCl$_3$) δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1 ) and the resultant solid was recrystallized from ethyl acetate/Hexane to yield the title compound as a white solid.

mp 97-98° C.

MS 257 (M$^{-1}$)

Elemental Analysis:

Anal Calc: C, 46.50; H, 5.46; N, 10.85; S, 12.41

Anal Found: C, 46.48; H, 5.65; N, 10.90; S, 12.07

$^1$H NMR (CDCl$_3$) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

EXAMPLE 7

(2S)-(−)-N-(6-Chloro-2,3-dihydro-benzo[1,4]dioxin-2-ylmethyl)-sulfamide (Compound #8)

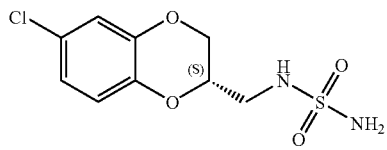

Following the procedure outlined in Example 4 above, 4-chlorocatechol was reacted to yield a mixture of (2S)—C-(7-Chloro-2,3-dihydro-benzo[1,4]dioxin-2-yl)-methylamine and (2S)—C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)—C-(6-Chloro-2,3-dihydro-benzo[1,4]dioxin-2-yl)-methylamine as an oil.

$[α]_D$=67.8 (c=1.51, CHCl$_3$)

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column using DCM/methanol 20:1 to yield the title compound as a white solid.

MS 277 (M$^{-1}$)

$[α]_D$=59.9° C.(c=1.1 1, M)

$^1$H NMR (CDCl$_3$) δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5 Hz, 1H), 4.05 (dd, J=7.1, 11.5 Hz, 1H), 3.45 (m, 2H)

Elemental Analysis:

Anal Calc: C, 38.78; H, 3.98; N, 10.05

Anal Found: C, 38.80; H, 3.67; N, 9.99.

The filtrates of the crystallized hydrochloride salt of (2S)—C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried (Na$_2$SO$_4$) and evaporated in vacuo to yield an oil, which was purified via reverse phase HPLC (10-50% ACN with 0.16% TFA in water with 0.20% TFA) to yield (2S)—C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 (M$^{-1}$)

$^1$H NMR (CDCl$_3$/CD$_3$OD) δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

EXAMPLE 8

Chroman-2-ylmethylsulfamide (Compound #10)

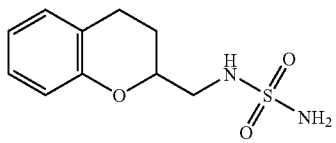

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16h. The reaction mixture was diluted with DCM (50 mL) and water (50 mL) and the pH of the mixture was adjusted to about pH=3.0 with 1N HCl. The DCM was separated and the aqueous phase extracted twice with DCM. The combined DCM phase was dried (Na$_2$SO$_4$) and evaporated in vacuo to yield an oil, which was purified with flash column chromatography (ethyl acetate) to yield an oil.

The oil (5.35 g, 30 mmol) in THF (90 mL) was stirred as 1M LAH in THF (36 mL, 36 mmol) was added and the reaction mixture was then stirred at room temperature for 20 h. The reaction was quenched with water, stirred for 2 hours, the solution decanted, dried (Na$_2$SO$_4$) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C.
MS 241 (M$^{-1}$)
Elemental Analysis:
Anal Calc: C, 49.57; H, 5.82; N, 11.56; S, 13.23
Anal Found: C, 49.57; H, 5.80; N, 11.75; S, 13.33.

EXAMPLE 9

2-(2,3-Dihydro-benzo[1,4]dioxin-2-yl)-ethylsulfamide (Compound #16)

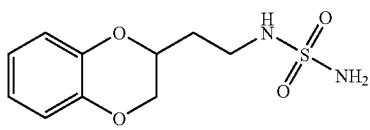 [SMILES: NS(=O)(=O)NCCC1COc2ccccc2O1]

Potassium cyanide (2.05 g, 31.5 mmol) was added to 2-bromomethyl-(2,3 dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried (Na$_2$SO$_4$) and evaporated in vacuo to yield 2-cyanomethyl-(2,3 dihydrobenzo[1,4]dioxine) as a white solid.

$^1$H NMR (CDCl$_3$) δ 6.89 (m, 4H), 4.50 (m, 1H), 4.31 (dd, J=2.3, 11.5 Hz, 1H), 4.08 (dd, J=6.2, 11.6 Hz, 1H), 2.78 (d, J=6.1, Hz, 2H)

The 2-cyanomethyl-(2,3 dihydrobenzo[1,4]dioxine) was dissolved in THF (50 mL) and 1M BH$_3$ in THF (80 mL, 80 mmol) was added and the reaction mixture refluxed for 5 h, then stirred at ambient temperature for 16 h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried (Na$_2$SO$_4$) and evaporated in vacuo to yield crude 2-(2,3 dihydrobenzo[1,4] dioxin-2-yl)ethylamine.

MS (M+H)$^+$180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM: MeOH—10:1) to yield a white solid. The solid was re-crystallized from DCM to yield the title compound as a solid.

MS (M-1) 257
MP 101-103° C. (corr)
$^1$H NMR (CDCl$_3$): δ 6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H).
Elemental Analysis:
Measured: C, 46.48; H, 5.60; N, 10.81; S, 12.41
Calculated: C, 46.50; H, 5.46; N, 10.85; S, 12.41

EXAMPLE 10

(2S)-(−)-N-(6,7 Dichloro-2,3-dihydro-benzo[1,4] dioxin-2-ylmethyl)-sulfamide (Compound #29)

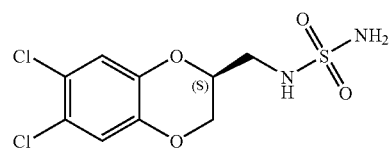

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried (MgSO$_4$) and evaporated in vacuo to yield a viscous oil of (2S)-2-(6,7-dichloro-2,3-dihydro-benzo[1,4]dioxine) methanol.

The (2S)-2-(6,7 dichloro-2,3-dihydro-benzo[1,4]dioxine) methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried (MgSO$_4$) and evaporated in vacuo to yield light yellow solid of toluene-4-sulfonic acid (2S)-6,7-dichloro-2,3-dihydro-benzo[1,4]dioxin-2-ylmethyl ester.

$^1$H NMR (CDCl3): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H), 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1 N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a viscous oil of (2S)-2-aminomethyl-(6,7-dichloro-2,3-dihydro-benzo[1,4]dioxine).

$^1$H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5Hz, 2H)

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.

MS [M–H]$^-$311.0
mp 119-121° C.
[α]$_D$=53.4° C.(c=1.17, M)
$^1$H NMR (DMSOd6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H)
Elemental Analysis:
Elemental Analysis:
Measured: C, 34.52; H, 3.22; N, 8.95; Cl, 22.64; S, 10.24
Calculated: C, 34.64; H, 2.68; N, 8.87; Cl, 22.94; S, 10.35.

EXAMPLE 11

(2S)-(–)-N-(7-Amino-2,3-dihydro-benzo[1,4]dioxin-2-ylmethyl)-sulfamide (Compound #36)

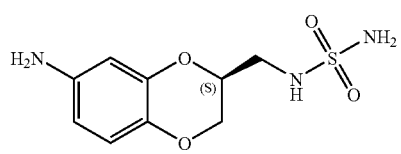

(2S)-(–)-N-(2,3-Dihydro-7-nitro-benzo[1,4]dioxin-2-ylmethyl)-sulfamide (1.2 g, 4.15 mmol), was prepared from 4-nitrocatechol according to the process outlined in Example 4. The (2S)-(–)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.

MS (M+H)$^+$260
$^1$H NMR (DMSO d6): δ 10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H)

EXAMPLE 12

(2S)-(–)-N-(7-Methyl-2,3-dihydro-benzo[1,4]dioxin-2-ylmethyl)-sulfamide (Compound #19)

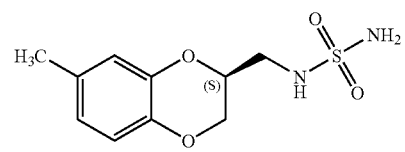

Title compound was prepared according to the procedure described in Example 4 above, starting with 4-methylcatechol, to yield a white solid, which was recrystallized from ethyl acetate/hexane to yield the title compound as a white solid.

MS [M–H]$^-$257
$^1$H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H).
Elemental Analysis
Calculated: C, 46.50; H, 5.46; N, 10.85; S, 12.41
Found: C, 46.65; H, 5.60; N, 10.84; S, 12.61.

EXAMPLE 13

Mouse Formalin Assay (NINDS)

The mouse formalin test is an acute and chronic model for testing the ability of a test compound for the treatment of pain.

In the Mouse Formalin Test, 0.5% formalin was injected s.c. into the plantar region of the hind-paw of adult male mice to induce an inflammatory-mediated pain response. Pain was expressed as licking of the injected area in a bi-modal manner—acute and chronic phase. The acute phase occurred immediately and lasted approximately 20 min post-injection, representing direct stimulation of pain fibers. Licking behavior resumes approximately 10 mins later (~20 min post injection) and lasted 10-15 min, representing the chronic phase hypothesized to be caused by the release of inflammatory mediators such as cytokines.

Activity in the acute phase of the formalin test is an indicator of acute pain believed to correlate with peripheral pain pathways. Activity in the chronic phase of the formalin test is indicative for a centralization and sensitization of pain at higher pain conducting pathways and has been shown to correlate well with efficacy in the Bennett chronic constriction model of neuropathic pain and clinical efficacy for chronic neuropathic pain (Vissers et al., 2003).

Compound #8 was evaluated in the Mouse Formalin Test as described above. Compound #8 was administered at 110 mg/kg, i.p. 15 min prior to formalin injection and was observed to significantly attenuate the acute and chronic phase responses. For the acute phase the decrease was 52% from control (p<0.01), while for the chronic phase the decrease was 43% from control (p<0.01). Compound #8 administered at 60 mg/kg i.p. exhibited similar analgesic activity, with a 30% decrease from control (p<0.05) for the acute phase and a 40% decrease from control (p<0.01) for the chronic phase.

Thus, in this assay, Compound #8 exhibited analgesic activity, particularly related to acute and chronic inflammatory pain.

EXAMPLE 14

Rat Chung Model of Neuropathic Pain

The rat Chung model is an assay used in determining whether a compound is useful for the treatment of neuropathic pain (Kim and Chung, 1994; Chaplan et al., 1994).

In this study, male Sprague Dawley rats (145-165 g; Harlan) were anesthetized and the L5 nerve was isolated and ligated with silk suture material resulting in mechanical allodynia. Six weeks post-ligation, the rats were dosed acutely with vehicle (an aqueous solution of 0.5% methylcellulose) or Compound #8 at 120 and 240 mg/kg, p.o. Mechanical (tactile) allodynia was quantified by recording the pressure at which the affected paw withdrew from a graded stimulus (von Frey hairs) at 30 min, 1, 2, 4, 6, 8 and 24 h post-dosing. The results were normalized and results are presented as % MPE (maximum protective effect) of the drug.

Treatment with Compound #8 at 120 mg/kg p.o. resulted in 42% increase in the %MPE relative to control animals. Efficacy was observed at 30 min, peaked at 1 h and was sustained at 4 h post-dosing. Treatment with Compound #8 at 240 mg/kg, po resulted in 66% increase in the %MPE relative to control animals. Efficacy was observed at 30 min, peaked at 2-4 h and was sustained at 24 h post-dosing. (Vehicle treated rats had no effect.)

Note that in this assay, gabapentin at 480 mg/kg p.o. dosing was used as a positive control. The effect of gabapentin was equivalent to the activity measured for Compound #8 at 240 mg/kg dosing.

Thus, in this assay, Compound #8 exhibited analgesic activity, particularly related to chronic inflammatory and/or neuropathic pain.

EXAMPLE 15-18

Lumbar 5 (L5) Spinal Nerve Ligation (Chung) Model of Neuropathic Pain

The rat Chung model is an assay used in determining whether a compound is useful for the treatment of neuropathic pain (Kim and Chung, 1994; Chaplan et al., 1994). In this assay, injury to the sciatic nerve by loose ligation with chromic gut suture, tight ligation of the L5 spinal nerve with silk suture or partial tight ligation with silk suture each produces hypersensitivity to many stimulus modalities (e.g., touch, pressure, temperature) that lasts for weeks or months. Hypersensitivity produced by such injuries is reminiscent of allodynia and hyperalgesia observed in clinical conditions of neuropathic pain caused by mechanical nerve injury, diabetes and chemotherapy. This assay is predictive of analgesic, antiallodynic and/or antihyperalgesic effect of test compounds.

Test compound and controls were dissolved in the appropriate volume of 0.5% HPMC or 10% solutol in 0.5% hydoxypropyl methylcellulose (HPMC). HPMC served as the vehicle for preparation of gabapentin solutions used as the positive control. Solutions were prepared to provide the final dose in a volume of 2.5 mL/kg or 5 mL/kg p.o. for rats. Male, Sprague-Dawley rats from Harlan Industries (Indianapolis, Ind.), weighing 150 to 250 grams at the time of surgery, were used for $L_5$ SNL studies.

All animals had a week quarantine/acclimation period before being transferred to a general stockroom. Rats in the SNL studies were housed and tested in the same room. Animals were housed in micro-isolator cages in groups of four rats per cage or 5 mice per cage with corncob bedding and free access to food and water. The environment was maintained at a constant temperature of 21° C., with a 12-hour light/dark cycle. Rats undergoing $L_5$ SNL surgery were placed into individual housing cages with alpha dry bedding and had access to enrichment food, food pellets and water ad libitum. Animals were allowed four to six weeks recovery from surgery prior to testing and were not tested beyond eight weeks post-surgery. For $L_5$ SNL testing, only those animals that responded to less than 4 gr force were included in further testing and analysis, being randomized into treatment groups on the day of study. In all tests, the investigator performing the behavioral analysis was blinded to the treatment administered to any individual animal.

For $L_5$ SNL surgery, rats were induced and maintained on isoflurane inhalation anesthesia. A 2-cm skin incision was made just left of midline over the dorsal aspect of the $L_4$-$S_2$ spinal segments, followed by separation of the paraspinal muscles from spinous processes. The transverse process of $L_6$ was then carefully removed and the $L_5$ spinal nerve was identified. The left $L_5$ spinal nerve was then ligated tightly with 6-0 silk thread, the muscle was sutured with 4-0 vicryl, and the skin was closed with wound clips.

Behavioral testing was performed on $L_5$SNL rats at a time between 3-6 weeks post-ligation. On the day of study, following baseline von Frey determinations to verify the presence of mechanical allodynia, $L_5$ SNL rats were orally dosed with vehicle, Compound #8 or gabapentin (as a positive control). Tactile allodynia was quantified at 30 min, 1 hr, 2 hrs, 4 hrs, 6 hrs, 8 hrs and/or 24 hr post-dosing by recording the force at which the paw ipsilateral to the nerve ligation was withdrawn from the application of a series of calibrated von Frey filaments (0.4, 0.7, 1.2, 2.0, 3.6, 5.5, 8.5 and 15.1 g; Stoelting; Wood Dale, Ill.). Beginning at an intermediate stiffness (2.0 g), filaments were applied to the mid-plantar hind paw for approximately 5 seconds. A brisk paw withdrawal led to the presentation of the next lighter stimulus and the lack of a withdrawal response led to the presentation of the next stronger stimulus to determine the response threshold. A total of four responses after the first threshold detection were collected. The 50% withdrawal thresholds were interpolated by the method of Dixon (as described in Meert T F and Vermeirsch, H A, *Pharmacol. Biochem. Behav.;* 2005, 80(2), pp 309-326) and when response thresholds fell above or below the range of detection, respective values of 15.0 or 0.25 g were assigned.

Threshold data from von Frey filament testing were reported as withdrawal threshold in grams or converted to percent maximal possible effect (%MPE), according to the formula: %MPE=[(post-drug threshold)−(baseline threshold)]/[(15-gr cut-off value)−(baseline threshold)]×100. The effective dose producing a 50% effect ($ED_{50}$) and associated statistics were calculated using PharmTools Plus software (The McCary Group). Statistics (two-way ANOVA) for the acetic acid assay were calculated using Graph Pad Prism v4.0. Data from time course studies in the SNL model of neuropathic pain were analyzed by a within-subjects, repeated measures, one-way ANOVA. Significant main effects (p<0.05) were further analyzed using Dunnett's multiple comparison test. Data are presented below as the mean±S.E.M. A number of studies were completed, with results as detailed below.

EXAMPLE 15

Study A

In a first study, Compound #8 was evaluated at 120 mg/kg and 240 mg/kg and compared with gabapentin at 480 mg/kg and vehicle.

In rats that had not had surgery, average withdrawal thresholds were greater than 13 g. Six weeks after surgery, withdrawal thresholds were between 1.0 and 1.6 g. Vehicle did not modify withdrawal thresholds over the 4 hour study period.

A dose of 480 mg/kg gabapentin significantly increased thresholds at the 1 hr, 2 hrs, and 4 hrs times post-dosing (73.2±14.7 and 73.7±16.6% reversal at 2 hrs and 4 hrs, respectively). The effect of dosing with Compound #8 at 120 mg/kg Compound #8 was slightly lower than those observed with gabapentin, but was significantly different from baseline (time '0') at 1 hr (42.2±13.8% reversal) and 4 hrs (45.4±12.2% reversal) after oral administration. Dosing at 240 mg/kg of Compound #8 produced effects (65.6±21.1% change at 4 hr) similar to those observed with gabapentin (73.4±15.2 at 4 hr). Thus, both gabapentin and Compound #8 significantly increased withdrawal thresholds at 2 hrs, 4 hrs and 6 hrs after oral administration. Effects waned by 8 hrs and were similar to vehicle-treated values 24 hr after administration.

EXAMPLE 16

Study B

In a second study, daily administration of Compound #8 for 7 days was evaluated to determine whether sub-chronic dosing would alter withdrawal thresholds. Three weeks after surgery, baseline tactile hypersensitivity was assessed. Rats were randomized into 5 groups and received vehicle (HPMC), 60 mg/kg, 120 mg/kg, 240 mg/kg or 480 mg/kg of Compound #8. Withdrawal thresholds were evaluated at 1 hr, 2 hrs, 4 hrs, 8 hrs and 24 hrs after dosing on Day 1 (initial dose), Day 3 (third dose) and Day 7 (seventh dose).

Following the first administration of Compound #8, 480 mg/kg produced a significant reversal in tactile hypersensitivity, with the peak effect occurring 4 hrs after dosing (64.3±9.9% reversal). No significant differences were observed in the other treatment groups at this time point, although there were non-statistically significant trends for lower doses of Compound #8 to reverse tactile hypersensitivity. On the third and seventh day of dosing, none of the treatment groups exhibited a significant reversal of tactile hypersensitivity.

EXAMPLE 17

Study C

In a third study, Compound #8 was administered at 100 mg/kg, 300 mg/kg and 560 mg/kg, p.o., gabapentin was administered as a positive control at 560 mg/kg and mechanical allodynia was measured at 2 hrs, 4 hrs and 6 hrs post-dosing, at 4 weeks after surgery.

In this study, treatment with Compound #8 at 100 mg/kg, 300 mg/kg or 560 mg/kg, p.o. did not show a statistically significant effect up to 6 hrs. Dosing with gabapentin at 560 mg/kg (positive control) resulted in an observed decrease in mechanical allodynia at 2 hrs and 4 hrs post dosing (58.7 and 86.4% reversal, respectively) relative to baseline, but not at 6 hrs post dosing. (Note that this behavior with gabapentin does not appear to be consistent with the expected behavior of gabapentin in the Chung model.)

EXAMPLE 18

Study D

In a fourth study, the effect of Compound #8 at 560 mg/kg dose using a 10% solutol in HPMC solution was evaluated. Gabapentin was administered as a positive control at 560 mg/kg and mechanical allodynia was measured at selected time points up to 6 h post-dosing.

Four weeks after surgery, vehicle (10% solutol in HPMC), Compound #8 at 560 mg/kg or gabapentin at 560 mg/kg was orally administered to rats. In this study, vehicle produced a statistically significant increase in tactile hypersensitivity compared with baseline over the duration of the study, while gabapentin produced a statistically significant decrease (55 to 77% reversal) in tactile hypersensitivity at between 2 hrs and 6 hrs after administration. There was a non-statistically significant trend for rats dosed with Compound #8 with a decrease in hypersensitivity between 4 hrs and 6 hrs after administration. More specifically, treatment with Compound #8 at 560 mg/kg p.o. showed a decrease in mechanical allodynia at 4 hrs and 6 hrs post dosing, but with a p=0.054.

Note that the effect of the positive control was variable in each of the above described studies in the Chung model. Therefore the effect of Compound #8 should be interpreted in context with the positive control response for any given study.

EXAMPLE 19

Taxol® Induced Peripheral Neuropathy Model

Peripheral neuropathies are chronic conditions that arise when nerves are damaged by trauma, disease, metabolic insufficiency or by certain drugs and toxins. The sensory disturbances associated with chemotherapeutic agents, such as paclitaxel (Taxol®), range from mild tingling to spontaneous burning, typically in the hands and feet. Symptoms become more intense with continued therapy and can lead to weakness, ataxia, numbness and pain that can take weeks to months to resolve.

In a pilot study, Compound #8 was evaluated for its ability to reduce Taxol®-induced mechanical allodynia and neurodegeneration of the sciatic nerve (Polomano, R C, Mannes, A J, Clark, U S, Bennett, G J. A painful peripheral neuropathy in the rat produced by the chemotherapeutic drug, paclitaxel. Pain, 94: 293-304, 2001; Flatters, S J L, Xiao, W-H, Bennett, G J. Acetyl-L-carnitine prevents and reduces paclitaxel-induced painful peripheral neuropathy. Neurosci Lett 397:219-223, 2006). In addition, the compound's effects on spontaneous locomotor activity was measured.

Method:

Male Sprague-Dawley rats (recieved from Harlan Sprague Dawley, Inc. at 7 weeks old) were divided into two treatment groups (n=10/group): the first group was treated with 2 mg/kg Taxol®, i.p. +0.5% HPMC (hydroxypropylmethylcellulose) vehicle, po; the second group was treated with 2 mg/kg Taxol, i.p. +100 mg/kg Compound #8 (in HPMC vehicle), po.

The animals were housed in polycarbonate plastic cages, 2 animals per cage, at a temperature of 18-26° C., 30-70% humidity, 12-hour light/dark cycle, with food and water available ad libityum.

On days 1, 3, 5, and 7, the rats received an ip (intraperitoneal) injection of Taxol® (2 mg/kg). In addition, animals received daily po (oral) doses of Compound #8 or vehicle for 12 days, beginning on the first day of Taxol® injections.

Two behavioral tests were performed: measurement of tactile sensitivity and spontaneous locomotor activity. At baseline and on Days 5 and 12 post-Taxol® injection, the animals underwent Von Frey testing for mechanical allodynia (according to the procedure as described in Chaplan, S R, Bach, F W, Pogrel, J W, Chung, J M, Yaksh, T L. Quantitative assessment of tactile allodynia in the rat paw. J Neurosci Meth, 53:55-63, 1994). Tactile sensitivity (i.e. mechanical allodynia) was measured using calibrated filaments touched to the plantar surface of the affected limb to determine paw withdrawal threshold. Briefly, the rats were placed in a Plexiglas cage with a wire mesh bottom and allowed to acclimate for 10 minutes. Once the animals settled, the plantar surface of the right hind paw was touched with a 2.0 g von Frey filament. In the absence of a paw withdrawak response to the initially selected filament, a stronger stimulus was presented; in the event of paw withdrawal, the next weaker stimulus was chosen. In this fashion, the resulting pattern of positive and negative responses was used to determine paw withdrawal threshold. Data were analyzed using two-way ANOVA, one-way ANOVA and Dunnett's test, with statistical significance at $p<0.05$.

On Day 11 after the start of Taxol® injection, the animals underwent Open Field testing to measure motor activity levels. Previous studies have shown Taxol® treatment can lead to decreased spontaneous locomotor activity (e.g., number of beam crossings) (Pascual, D, Goicoechea, C, Suardiaz, M, Martin, Mich. A cannabinoid agonist, WIN 55,212-2, reduces neuropathic nociception induced by paclitaxel in rats. Pain 118: 23-34, 2005). The Open Field test was performed by placing the animal into a 17"×17" open chamber that contained infrared light strips that are positioned around the walls of the chamber. The light strips transmit infrared beams of light so that horizontal (locomotor) and vertical (rearing) movements of the animal are automatically recorded every 100 msec by beam breaks. For this study, the locomotor activity levels of the animal were recorded over a 20 min period of time to evaluate spontaneous activity in a novel environment. Data were analyzed using one-way ANOVA and Dunnett's test, with statistical significance at $p<0.05$.

On Day 13, the animals were euthanized by carbon dioxide asphyxiation. The sciatic nerve and right hind paw were excised and placed in 10% neutral buffered formalin. The harvested tissues were blocked, embedded in paraffin, sectioned and stained with hemotoxylin and eosin. The tissue was examined using light microscopy and scored by an evaluator blind to the treatment regimen. The tissue was ranked on a scale of 0 to 3 based on the degree and amount of axonal disruption observed in the section, with 0 being a normal appearance of the axon, 1 to 2 being a mild to moderate disruption of the axons and a 3 being a complete disruption and Wallerian degeneration of the axons (Cavaletti, G, Tredici, G, Braga, M, Tazzari, S. Experimental peripheral neuropathy induced in adult rats by repeated intraperitoneal administration of Taxol®. Exper Neurol 133:64-72,1995). Data were analyzed using one-way ANOVA and Dunnett's test, with statistical significance at $p<0.05$.

Results:

Mechanical allodynia was measured at baseline, Day 5 and Day 12 post-Taxol® administration. There was no significant difference between groups at baseline or Day 5; however, on Day 12 both the Taxol® alone ($p<0.05$) and Taxol®+100 mg/kg Compound #8 ($p<0.001$) treated groups were more pain-sensitive in comparison with their baseline responses. Compound #8 appeared to potentiate the pain response compared to Taxol® alone; however, this difference was not statistically significant.

Spontaneous locomotor activity was tested on Day 11 following the start of Taxol® dosing. There was no difference between treatment groups for horizontal movement; however, the Taxol®+Compound #8 ($p<0.05$) treated animals exhibited decreased vertical rearing compared to Taxol® alone.

Histopathological evaluation of sections of the right hindpaw and sciatic nerve were performed. Compound #8 had no effect on the severity of Taxol®-induced degeneration in the right hind paw; however, there was a positive trend to decreased degeneration in the sciatic nerve, although the differences were not statistically significant.

Discussion:

The pilot study was performed to evaluate the efficacy of Compound #8 on pain, movement changes and nerve damage that can occur as a result of Taxol®-induced peripheral neuropathy. Typically, rats treated with Taxol are evaluated several weeks post-injection because the resulting mechanical allodynia develops anywhere between 12 to 21 days post-Taxol®. In the present study, compound efficacy was evaluated on Days 5 and 12 post-Taxol®, a shorter study duration than previously published studies; however, it is noted that significant allodynia could occur within this timeframe.

The results suggest that on Day 12 mechanical allodynia was developed with Taxol® treatment, although the magnitude of the effect was not robust (baseline: 16.42±2.14 g, day 12: 12.11±4.92 g). However, Compound #8 was ineffective in preventing the allodynia at this same time point. This result is viewed as inconclusive. Increasing the time course of the study may have revealed a more pronounced effect of Taxol® and a protective effect of Compound #8. Additionally, it is noted that a positive control was not included in the study.

Assessment of open field behavior indicated that rats treated with Compound #8 exhibited decreased rearing behavior, compared to Taxol® alone, indicating a lower level of spontaneous vertical exploration. However, since the horizontal activity levels did not differ with Compound #8 treatment from that of the Taxol® alone group, pain or sedation are not likely reasons for the reduced rearing. The histopathological analysis revealed a trend toward reduction of sciatic nerve damage with treatment with Compound #8; however, it was not statistically significant.

Taken together, this preliminary study suggests that Compound #8 may have beneficial effects against Taxol®-induced peripheral neuropathy in rats. Proposed follow-up studies would include a longer testing period post-Taxol® (e.g., ~6 week time course) and multiple dosing levels (e.g. a dose-response curve) for Compound #8.

EXAMPLE 20

Taxol® Induced Peripheral Neuropathy Model

Peripheral neuropathies are chronic conditions that arise when nerves are damaged by trauma, disease, metabolic insufficiency or by certain drugs and toxins. The sensory disturbances associated with chemotherapeutic agents, such as paclitaxel (Taxol®), range from mild tingling to spontaneous burning, typically in the hands and feet. Symptoms become more intense with continued therapy and can lead to weakness, ataxia, numbness and pain that can take weeks to months to resolve.

A this second, longer term study using the Taxol® induced peripheral neuropathy model was completed as a follow-up to the preliminary study describe in Example 19 above.

Method:

Paclitaxel (Taxol®, Bristol-Myers-Squibb; 6 mg/ml in a 50:50 mixture of Cremophor and ethanol) was diluted just before use with saline to a concentration of 2 mg/ml and injected IP in a volume of 1 ml/kg) on four alternate days (D0, D2, D4, and D6). Compound #8 was suspended in 0.1N HCl:0.5% methylcellulose (1:9) immediately prior to each injection at concentrations of 60 mg/ml and 120 mg/ml.

Adult male Sprague-Dawley rats (Harlan, Indianapolis, Ind.; Frederick, Md. breeding colony) were caged on sawdust bedding in groups of 3-4 with food and water available ad libitum and a 12:12 hr light-dark cycle.

Three groups of paclitaxel-treated animals, each n=12, were formed:

Group 1 was treated with Compound #8 at 60 mg/kg, PO (oral gavage), daily for 20 days, starting on D0 (the same day as the beginning of paclitaxel dosing). On those days when both Compound #8 and paclitaxel were to be administered, Compound #8 was given at 0900 h and paclitaxel at 1300 h.

Group 2 was treated with Compound #8 at 120 mg/kg, PO (oral gavage), daily, starting on D0 (the same day as the beginning of paclitaxel dosing). On those days when both Compound #8 and paclitaxel were to be administered, Compound #8 was given at 0900 h and paclitaxel at 1300 h.

Group 3 was treated with an equal volume of vehicle, daily, starting on D0 (the same day as the beginning of paclitaxel dosing).

The animals were habituated to the testing environment on three separate days and then three daily baseline sessions were given to measure the normal response rate to stimulation with von Frey hairs exerting 4 g or 15 g of pressure (4 gVFH and 15 gVFH). Normal rats rarely, if ever, withdraw from stimulation with 4 gVFH; thus, a post-paclitaxel increase in responding to this stimulus is indicative of mechano-allodynia. Normal rats withdraw from stimulation with 15 gVFH 10-20% of the time; thus an increased response frequency to this stimulus is indicative of mechano-hyperalgesia.

The animals were positioned beneath upturned plastic mouse cages atop an elevated platform with wire-mesh flooring. Each VFH was applied to the glabrous skin of the mid-heel and the presence or absence of a withdrawal response was noted. This was repeated 5 times on each hind paw and the animal's responses were summarized as a percent response score (e.g., 5 withdrawal responses to 15gVFH stimulation would yield a score of 50%). Behavior was assessed by an observer who was blind as to group assignment.

Behavioral tests for paclitaxel's effects began on day 13 (D13) and were repeated on D15, D17, D21, D24, D28, D31, D35 and D38. The tests on days 13-17 were during the 20 day dosing period for Compound #8. For these days the drug was given at 0900 h and behavioral tests began at 1300 h. Significant paclitaxel-evoked mechano-allodynia and mechano-hyperalgesia were expected to develop 10-14 days after the last injection of paclitaxel.

Results:

As expected, paclitaxel-treated rats that received vehicle injections developed mechano-allodynia (4 gVFH test) and mechano-hyperalgesia (15 gVFH test).

Both 60 mg/kg and 120 mg/kg doses of Compound #8 suppressed the development of mechano-allodynia and mechano-hyperalgesia. The suppressive effect was apparent at the onset of the pain syndrome and continued for approximately 11 days after the last injection of Compound #8; allodynia and hyperalgesia returned thereafter. There were no significant differences between the two dosage groups. Compound #8 treatment produced no apparent side-effects. Block of mechano-allodynia appeared to be superior to block of mechano-hyperalgesia.

EXAMPLE 21

Acetic Acid-induced Abdominal Constriction Model of Visceral Pain

The purpose of this assay was to determine whether Compound #8 reverses hypersensitivity in visceral, inflammatory and neuropathic models of pain.

Test compound and controls were dissolved in the appropriate volume of 0.5% HPMC or 10% solutol in 0.5% hydoxypropyl methylcellulose (HPMC). HPMC served as the vehicle for preparation of gabapentin solutions used as the positive control. Solutions were prepared to provide the final dose in a volume of 10 mL/kg orally (p.o.) for mice. Male CD-1 mice from Charles Rivers Laboratories (Portage, Me.), weighing between 25 and 30 grams at the time of study, were used for the acetic acid-induced abdominal stretching studies.

All animals had a week quarantine/acclimation period before being transferred to a general stockroom. Mice in the acetic acid-induced abdominal stretching study were allowed 1 hr to acclimate to the testing room before the start of the study. Animals were housed in micro-isolator cages in groups of four rats per cage or 5 mice per cage with corncob bedding and free access to food and water. The environment was maintained at a constant temperature of 21° C., with a 12-hour light/dark cycle.

Animals used in the acetic acid-induced abdominal stretching test were maintained with original cage mates throughout the study period (four rats per cage, 5 mice per cage; cages were Nalgene® with corn cob bedding). Animals from several cages were randomly assigned across treatment groups; that is, mice in a given cage were pseudo-randomly assigned to different treatment groups. In all tests, the investigator performing the behavioral analysis was blinded to the treatment administered to any individual animal.

On the day of study, mice were orally dosed either with vehicle (Methocel or 10% Solutol:Methocel), 560 mg/kg of Compound #8 or 560 mg/kg of gabapentin as a positive control. Mice were then given an i.p injection of 0.5 mL (2×0.25 mL/abdominal quadrant) of 0.6% acetic acid following 1 hr, 2 hrs, 3 hrs or 4 hours treatment with vehicle, compound or positive control. Five minutes after i.p acetic acid injection, 5 animals were placed into separate bell jars containing a small amount of bedding chips, and the number of abdominal stretches per animal was recorded for 5 minutes. This was repeated for each group (N=10 mice/group).

The effective dose producing a 50% effect ($ED_{50}$) and associated statistics were calculated using PharmTools Plus software (The McCary Group). Statistics (two-way ANOVA) for the acetic acid assay were calculated using Graph Pad Prism v4.0. Data from the acetic acid-induced model of visceral pain were analyzed by a 2-way analyses of variance (ANOVA). Significant main effects ($p<0.05$) were further analyzed using Dunnett's multiple comparison test. Data are presented below as the mean±standard error of the mean (S.E.M.).

Compound #8 was evaluated in the acetic acid induced-model of viscero-chemical pain. In vehicle-treated mice, the average number of abdominal stretches was between 13 and 16.2 among the 4 groups. Although gabapentin tended to decrease the number of stretches at 2 hr (11.00±1.5 stretches) and 3 hr (10.0±1.6 stretches) after oral administration, this effect was not statistically significant. Compared with vehicle- or gabapentin-treated mice, treatment with 560 mg/kg of Compound #8 did not significantly modify acetic acid-induced stretching.

Compound #8 did not modify abdominal constrictions produced by an i.p. injection of acetic acid. Similarly, gabapentin did not significantly decrease acetic acid-induced constrictions. These results suggest that this assay may not be sensitive to analgesic effects of these anti-convulsant compounds.

EXAMPLE 22

Complete Freund's Adjuvant (CFA)-induced Model of Inflammatory Pain

Intraplantar injection of CFA in rats results in a long-lasting inflammatory reaction, characterized by edema and a pronounced hypersensitivity to both thermal and mechanical stimuli. This hypersensitivity peaks between 24-72 hours after injection and can last for several weeks. This assay predicts the analgesic, antiallodynic and/or antihyperalgesic effect of test compounds.

Test compound and controls were dissolved in the appropriate volume of 0.5% HPMC or 10% solutol in 0.5% hydoxypropyl methylcellulose (HPMC). Solutions were prepared to provide the final dose in a volume of 2.5 mL/kg or 5 mL/kg p.o. for rats. Male, Sprague-Dawley rats from Charles Rivers Laboratories (Portage, Me.), weighing between 250 and 350 grams at the time of study, were used for the CFA paw radiant heat studies.

All animals had a week quarantine/acclimation period before being transferred to a general stockroom. Rats in the CFA study were moved to a testing room the day of the CFA injection, where they remained for the duration of the study. Animals were housed in micro-isolator cages in groups of four rats per cage or 5 mice per cage with corncob bedding and free access to food and water. The environment was maintained at a constant temperature of 21° C., with a 12-hour light/dark cycle.

Animals used in rat CFA-RH tests were maintained with original cage mates throughout the study period (four rats per cage, 5 mice per cage; cages were Nalgene® with corn cob bedding). Animals from several cages were randomly assigned across treatment groups; that is, rodents in a given cage were pseudo-randomly assigned to different treatment groups. For CFA testing, only rats that exhibited at least a 25% reduction in response latency from baseline (i.e., hyperalgesia) were included in further testing and analysis. In all tests, the investigator performing the behavioral analysis was blinded to the treatment administered to any individual animal.

On the day of study, rats were given a 100 μL (1 μg/μL) intraplantar injection of CFA (1:1 CFA:saline) into their left hindpaw. Following a 24 hour incubation period, response latencies on a radiant heat paw stimulator (RH) were obtained and compared to baseline (pre-CFA) latencies. The response was automatically registered by the RH device when the rat lifted its paw from the surface of the glass. Following the post-CFA latency assessment, rats were dosed orally (2.5 mL/kg) with Compound #8 or vehicle (HPMC). Percent Reversal of hyperalgesia was calculated for each animal as [(treatment response)−(post-CFA response)]/[(pre-CFA response)−(post-CFA response)]×100. Average % reversal of hyperalgesia was then calculated for each treatment group (n=5-6 rats/group).

The effective dose producing a 50% effect ($ED_{50}$) and associated statistics were calculated using PharmTools Plus software (The McCary Group). Statistics (two-way ANOVA) for the acetic acid assay were calculated using Graph Pad Prism v4.0. Data from time course studies in the CFA-induced model of inflammatory pain were analyzed by a within-subjects, repeated measures, one-way ANOVA. Significant main effects ($p<0.05$) were further analyzed using Dunnett's multiple comparison test. Data are presented below as the mean±S.E.M.

Compound #8 was evaluated in the CFA model of inflammatory pain. In normal rats, average paw withdrawal latencies were between 14.6 and 15.6 sec. Twenty-four hour after CFA, average paw withdrawal latencies had increased to between 6.0 and 6.8 sec, indicating that thermal hypersensitivity had developed. The oral administration of vehicle did not significantly modify paw withdrawal latencies. By comparison, an orally administered dose of 560 mg/kg gabapentin time-dependently reversed thermal hypersensitivity, with a peak 68.6% reversal (compared with the 24-hr post-CFA baseline) observed 4 hr after oral administration. An oral dose of 560 mg/kg of Compound #8 also time-dependently reversed thermal hypersensitivity, with a peak 86.0% reversal (compared with the 24-hr post-CFA baseline) observed 4 hr after oral administration.

Compound #8 time-dependently attenuated CFA induced thermal hypersensitivity indicating that compound #8 would be expected to be useful for treating inflammatory pain.

EXAMPLE 23

Formalin-Induced Hyperalgesia Model

Adult male CF-1 mice weighing 2-0 g were obtained from Charles River (Wilmington, Mass.). All animals were house on a 12:12 light:dark cycle and permitted free access to both food and water, except when removed from the home cage for experimental procedures.

Compound #8 was triturated in a small volume of 0.5% methylcelllulose, sonicated for 10 min and brought to a final volume with 0.5% methylcellulose. Compound # 8 was administered i.p. in a volume of 0.01 mL/1 0 g body weight to the test mice. Two hours after i.p. administration of Compound #8 or vehicle, an injection of 0.5% formalin was made into the plantar region of the right hind paw.

In this model, the injection of formalin elicits a distinct biphasic behavioral profile characterized by the mouse licking the affected paw. Immediately after the injection, the mouse licks the paw for about 10 minutes. This corresponds to phase 1 (acute response) and is followed by a brief latency period where there is little behavioral activity. A more prolonged period of about 20-30 minutes of paw licking ensues which constitutes phase 2 (inflammatory).

Prior to the administration of Compound #8 at 15 mg/kg (n=8), 30 mg/kg (n=8), 200 mg/kg (n=8), 300 mg/kg (n=4) or vehicle (n=8), each mouse underwent a 15-minute conditioning period in one of several 6" tall Plexiglas tubes (4" in diameter) that were placed in front of a mirror. Following the conditioning period, Compound #8 or vehicle was administered i.p. and the mouse returned to tits home tube. Two hours after administration, formalin was injected sub-dermally (20 μL, 27 gauge needle) into the plantar surface of the right hind foot. The bevel of the needle was placed facing down toward the skin surface. Following the injection of the formalin each animal was observed for the first 2 minutes of each 5 minute period for a total of 45 minutes. The cumulative length of licking for each 2 minute period was recorded. An animal receiving the requisite volume of vehicle was alternated with each mouse dosed with Compound #8. Animals were euthanized following the conclusion of the experiment.

Area under the curve (AUC) determinations were made using the GraphPad Prism Version 3.03. Total AUC was calculated for both the dosed and control groups for both acute and inflammatory phases. The AUC of individual animals for each phase was also calculated and converted to a percentage of total AUC of control. Average percentages and SEM for both Compound #8 dosed and vehicle dosing was calculated and tested for statistical significance.

Compound #8 was effective against acute, phase 1 pain associated with injection of formalin. For this components, the median effective dose ($ED_{50}$) and 95% confidence interval (CI) for producing a 50% or greater reduction in AUC was calculated to be 111 mg/kg (with a range of 62.0-245 mg/kg) following i.p. administration.

Compound #8 decreased the secondary phase of formalin-induced hyperalgesia in a dose-dependent manner. The median effective dose ($ED_{50}$) and 95% confidence interval (CI) for producing a 50% or greater reduction in AUC was calculated to be 101 mg/kg (with a range of 53.6-225 mg/kg) following i.p. administration.

The results from this study indicate that Compound #8 possesses the ability to reduce formalin-induced hyperalgesia, and indicates that Compound #8 would be expected to be useful for the treatment of acute and chronic inflammatory pain.

EXAMPLE 24

Compound #8 prepared as in Example 7 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for treating neuropathic pain, comprising administering to a subject in need thereof, a therapeutically effective amount of a compound of formula (I)

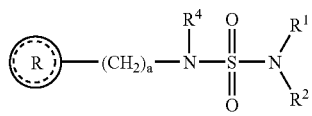

wherein $R^1$ and $R^2$ are each independently selected from the group consisting of hydrogen and methyl;

$R^4$ is selected from the group consisting of hydrogen and methyl;

a is an integer from 1 to 2;

is selected from the group consisting of

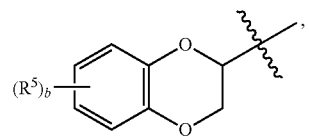

wherein b is an integer from 0 to 2;
each $R^5$ is independently selected from the group consisting of halogen, and lower alkyl;
or a pharmaceutically acceptable salt thereof.

2. The method as in claim 1, wherein

is selected from the group consisting of 2-(2,3-dihydro-benzo[1,4]dioxinyl), 2-(6-chloro-2,3-dihydro-benzo[1,4]dioxinyl), 2-(5-fluoro-2,3-dihydro-benzo[1,4]dioxinyl), 2-(7-chloro-2,3-dihydro-benzo [1,4]dioxinyl), 2-(7 methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), and 2-(8-chloro-2,3-dihydro-benzo[1,4]dioxinyl);
or a pharmaceutically acceptable salt thereof.

3. The method as in claim 2, wherein

is selected from the group consisting of 2 (2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);
or a pharmaceutically acceptable salt thereof.

4. The method of claim 1, wherein the compound of formula (I) is selected from the group consisting of (2S)-(-)-N-(6-chloro-2,3-dihydro-benzo[1,4]dioxin-2-ylmethyl)-sulfamide; and pharmaceutically acceptable salts thereof.

5. A method of treating neuropathic pain, comprising administering to a subject in need thereof a therapeutically effective amount of a compound selected from the group consisting (2S)-(-)-N-(6-chloro-2,3-dihydro-benzo[1,4]dioxin-2-ylmethyl)-sulfamide; and pharmaceutically acceptable salts thereof.

6. The method of claim 1, wherein the neuropathic pain is diabetic neuropathy.

7. The method of claim 5, wherein the neuropathic pain is diabetic neuropathy.

8. A method for the treatment of neuropathic pain, comprising administering to a subject in need thereof a therapeutically effective amount of a compound of formula

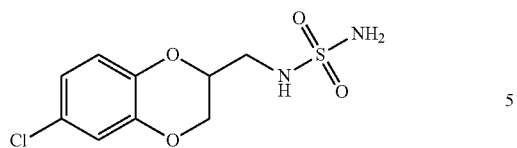
or a pharmaceutically acceptable salt thereof.
9. The method of claim 8, wherein the neuropathic pain is diabetic neuropathy.
* * * * *

UNITED STATES PATENT AND TRADEMARK OFFICE
CERTIFICATE OF CORRECTION

PATENT NO.        : 8,716,231 B2
APPLICATION NO.   : 11/612071
DATED             : May 6, 2014
INVENTOR(S)       : Smith-Swintosky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Eighteenth Day of August, 2015

Michelle K. Lee
*Director of the United States Patent and Trademark Office*